United States Patent
Ito

(10) Patent No.: US 11,324,560 B2
(45) Date of Patent: May 10, 2022

(54) SURGICAL INSTRUMENT

(71) Applicant: MEDICAROID CORPORATION, Kobe (JP)

(72) Inventor: Tetsushi Ito, Kobe (JP)

(73) Assignee: MEDICAROID CORPORATION, Kobe (JP)

(*) Notice: Subject to any disclaimer, the term of this patent is extended or adjusted under 35 U.S.C. 154(b) by 169 days.

(21) Appl. No.: 16/749,992

(22) Filed: Jan. 23, 2020

(65) Prior Publication Data

US 2020/0237463 A1    Jul. 30, 2020

(30) Foreign Application Priority Data

Jan. 25, 2019    (JP) .............................. JP2019-011557

(51) Int. Cl.
*A61B 34/00*      (2016.01)
*A61B 17/29*      (2006.01)
*A61B 34/30*      (2016.01)
*A61B 17/068*     (2006.01)
*A61B 17/3201*    (2006.01)
(Continued)

(52) U.S. Cl.
CPC .............. *A61B 34/71* (2016.02); *A61B 17/29* (2013.01); *A61B 17/068* (2013.01); *A61B 17/3201* (2013.01); *A61B 2017/00358* (2013.01); *A61B 2017/2808* (2013.01); *A61B 2017/2908* (2013.01); *A61B 2018/1412* (2013.01); *A61B 2018/1422* (2013.01); *A61B 2034/306* (2016.02); *A61B 2034/715* (2016.02)

(58) Field of Classification Search
CPC ....... A61B 34/71; A61B 17/29; A61B 17/068; A61B 17/3201; A61B 2034/306; A61B 2034/715; A61B 2017/00358; A61B 2017/2808; A61B 2017/2908; A61B 2018/1412; A61B 2018/1422

See application file for complete search history.

(56) References Cited

U.S. PATENT DOCUMENTS 9,101,379 B2    8/2015  Au et al.
9,259,274 B2    2/2016  Prisco
(Continued)

FOREIGN PATENT DOCUMENTS

JP    2003-24336 A    1/2003
JP    2015-535191 A   12/2015
(Continued)

*Primary Examiner* — Brooke Nicole Labranche
(74) *Attorney, Agent, or Firm* — Metrolex IP Law Group, PLLC

(57) ABSTRACT

A surgical instrument according to one or more embodiments may include: a base; an end effector; an elongated element to drive the end effector; a flexible shaft including a distal end coupled with the end effector; a winding member provided to the base rotatably about a rotational axis orthogonal to the second surface such that the elongated element from the flexible shaft is wound around the winding member; a drive receiving member rotatable about a rotational axis orthogonal to the second surface, to receive drive for rotating the winding member; a first guide pulley; and a second guide pulley. The first guide pulley guides the elongated element drawn from the shaft toward the second guide pulley along the rotational axis of the winding member, and the second guide pulley guides the elongated element from the first guide pulley toward the winding member in a direction intersecting the rotational axis.

14 Claims, 7 Drawing Sheets

(51) Int. Cl.
  *A61B 17/00* (2006.01)
  *A61B 17/28* (2006.01)
  *A61B 18/14* (2006.01)

(56) References Cited

U.S. PATENT DOCUMENTS

| | | |
|---|---|---|
| 9,743,990 B2 | 8/2017 | Au et al. |
| 9,931,106 B2 | 4/2018 | Au et al. |
| 10,022,194 B2 | 7/2018 | Prisco |
| 2017/0304014 A1 | 10/2017 | Au et al. |
| 2018/0193007 A1 | 7/2018 | Au et al. |
| 2018/0200895 A1 | 7/2018 | Kan |
| 2018/0214220 A1 | 8/2018 | Kan |
| 2018/0214226 A1 | 8/2018 | Kan |
| 2018/0311001 A1 | 11/2018 | Prisco |
| 2018/0370045 A1 | 12/2018 | Kan |
| 2019/0159852 A1 | 5/2019 | Ito et al. |
| 2019/0159854 A1 | 5/2019 | Ito |
| 2019/0201149 A1 | 7/2019 | Ito et al. |

FOREIGN PATENT DOCUMENTS

| | | |
|---|---|---|
| WO | 2012/068156 A2 | 5/2012 |
| WO | 2012/068156 A3 | 5/2012 |
| WO | 2018/013313 A1 | 1/2018 |
| WO | 2018/174226 A1 | 9/2018 |
| WO | 2018/174227 A1 | 9/2018 |
| WO | 2018/174228 A1 | 9/2018 |

SURGICAL INSTRUMENT

CROSS REFERENCE TO RELATED APPLICATIONS

This application claims priority to Japanese Patent Application No. 2019-011557 filed on Jan. 25, 2019, the entire contents of which are incorporated herein by reference.

BACKGROUND

The disclosure may relate to a surgical instrument, and particularly relate to a surgical instrument in which an end effector is driven through an elongated element.

In a related art, a robotic surgical system for supporting a surgery has been known. Such a robotic surgical system typically includes a patient-side apparatus and a remote operation apparatus for remotely operating the patient-side apparatus. An endoscope for visualizing the body cavity of a patient through image capturing, and a surgical instrument including an end effector for performing treatment on the patient are attached to the patient-side apparatus. The doctor performs an endoscopic surgery on the patient by operating the patient-side apparatus through the remote operation apparatus while checking an image of the patient through the endoscope. With the robotic surgical system, it is possible to reduce the size of a wound formed by incision of the skin of the patient, thereby performing a less invasive surgery with a reduced load on the patient.

For example, Japanese Translation of PCT International Application Publication No. 2015-535191 (Patent Document 1) discloses a surgical instrument used in such a robotic surgical system. The medical equipment (surgical instrument) disclosed in Patent Document 1 drives an end effector through a tendon (elongated element (such as a wire)). In the medical equipment, the tendon extends through the inside of a shaft. One end of the tendon, as an end of the tendon on a distal side of the shaft, is connected with the end effector, and the other end of the tendon, as an end of the tendon on a proximal side of the shaft, is wound around a capstan as a rotation member. In this medical equipment, the end effector is driven as the capstan is rotated by a driving motor to pull or feed out the tendon.

SUMMARY

In the surgical instrument disclosed in Patent Document 1, when the end effector is driven by the tendon, the axis of the capstan around which the tendon is wound is arranged to intersect the longitudinal direction of the surgical instrument. In this case, it may be difficult to mount the surgical instrument on the driving apparatus only by moving the surgical instrument in a direction along the longitudinal direction.

An object of an aspect of one or more embodiments may be to make it possible to easily mount a surgical instrument on a driving apparatus by moving the surgical instrument in a direction along the longitudinal direction of the surgical instrument.

A first aspect of one or more embodiments may be a surgical instrument that may include: a base with a first surface and a second surface; an end effector; an elongated element to drive the end effector; a flexible shaft with a distal end and a proximal end, the distal end being coupled with the end effector; a winding member that is provided to the base rotatably about a rotational axis orthogonal to the second surface and includes a part protruded from the first surface such that the elongated element drawn from the flexible shaft is wound around and fixed to the part of the winding member; a drive receiving member that is provided to face the second surface and be rotatable about a rotational axis orthogonal to the second surface, and is configured to receive drive for rotating the winding member; a first guide pulley that is arranged between the proximal end of the flexible shaft and the winding member and guides the elongated element; and a second guide pulley that is arranged between the first guide pulley and the winding member and guides the elongated element. The first guide pulley guides the elongated element drawn from the proximal end of the shaft toward the second guide pulley in a direction along the rotational axis of the winding member. The second guide pulley guides the elongated element guided by the first guide pulley toward the winding member in a direction intersecting the rotational axis of the winding member.

According to the first aspect, drive of a driving apparatus can be received from the second surface side of the base, and the surgical instrument can be easily mounted on the driving apparatus by moving the surgical instrument in a direction along the longitudinal direction of the surgical instrument.

A second aspect of one or more embodiments may be a surgical instrument that may include: a base with a first surface and a second surface; an end effector that includes a wrist part; an elongated element to drive the end effector; a flexible torque transferring member with a first end and a second end, the first end being coupled with the wrist part; a flexible shaft with a distal end and a proximal end, the distal end being coupled with the end effector; a winding member that is provided to the base rotatably about a first rotational axis orthogonal to the second surface and includes a part protruded from the first surface such that the elongated element drawn from the flexible shaft is wound around and fixed to the part of the winding member; a first drive receiving member that is provided to face the second surface and be rotatable about a second rotational axis orthogonal to the second surface, and receives drive for rotating the winding member; a first guide pulley that is arranged between the proximal end of the flexible shaft and the winding member and guides the elongated element; a second guide pulley that is arranged between the first guide pulley and the winding member and guides the elongated element; a coupling member that is provided to the base rotatably about a third rotational axis orthogonal to the second surface and is coupled with the second end of the torque transferring member; a second drive receiving member that is arranged to face the second surface and be coaxial with the coupling member, and is configured to receive drive for rotating the coupling member; and a gear member that is provided to be rotatable coaxially with the coupling member and is configure to transfer rotation of the first drive receiving member to the winding member.

According to the second aspect, drive of a driving apparatus can be received from the second surface side of the base, and the surgical instrument can be easily mounted on the driving apparatus by moving the surgical instrument in the direction along the longitudinal direction of the surgical instrument. In addition, surfaces that receive drive of the respective drive receiving members can be provided at the second surface, and thus the positions of the surfaces that receive drive of the respective drive receiving members can be aligned with each other. As a result, the configuration (structure) of the surgical instrument can be simplified. In addition, the surgical instrument can be further downsized along with the simplification of the configuration (structure).

A third aspect of one or more embodiments may be a surgical instrument that may include: a base with a first surface and a second surface; an end effector including a first jaw and a second jaw; a first elongated element including first and second parts to drive the first jaw; a second elongated element including a third part and a fourth part to drive the second jaw; a flexible shaft with a distal end and a proximal end, the distal end being coupled with the end effector; a first winding member that is provided to the base rotatably about a first rotational axis orthogonal to the second surface and includes a part protruded from the first surface such that the first and second parts of the first elongated element drawn from the flexible shaft are wound around and fixed to the protruded part of the first winding member; a second winding member that is provided to the base to be rotatable about a second rotational axis orthogonal to the second surface and includes a part protruded from the first surface such that the third and fourth parts of the second elongated element drawn from the flexible shaft are wound around and fixed to the protruded part of the second winding member; first and second guide pulleys that are arranged between the proximal end of the flexible shaft and the first winding member and guide the first part of the first elongated element; third and fourth guide pulleys that are arranged between the proximal end of the flexible shaft and the first winding member and guide the second part of the first elongated element; fifth and sixth guide pulleys that are arranged between the proximal end of the flexible shaft and the second winding member and guide the third part of the second elongated element; and seventh and eighth guide pulleys that are arranged between the proximal end of the flexible shaft and the second winding member and guide the fourth part of the second elongated element. A distance between the first part of the first elongated element guided by the first and second guide pulleys and the second part of the first elongated element guided by the third and fourth guide pulleys is larger than a distance between the first part of the first elongated element guided by the first and second guide pulleys and the third part of the second elongated element of guided by the fifth and sixth guide pulleys.

According to the third aspect, drive of a driving apparatus can be received from the second surface side of the base, and the surgical instrument can be easily mounted on the driving apparatus by moving the surgical instrument in the direction along the longitudinal direction of the surgical instrument. In addition, since the distance between two elongated elements provided to sandwich the winding member can be larger than the distance between two elongated elements provided not to sandwich the winding member, a space for providing the winding member can be easily obtained between the two elongated elements provided to sandwich the winding member. As a result, increase in the size of the surgical instrument due to the elongated elements can be prevented while the space for providing the winding member is easily obtained.

According to at least one of the above aspects, it is possible to easily mount the surgical instrument on the driving apparatus by moving the surgical instrument in a direction along the longitudinal direction of the surgical instrument.

DETAILED DESCRIPTION

Figure 1:
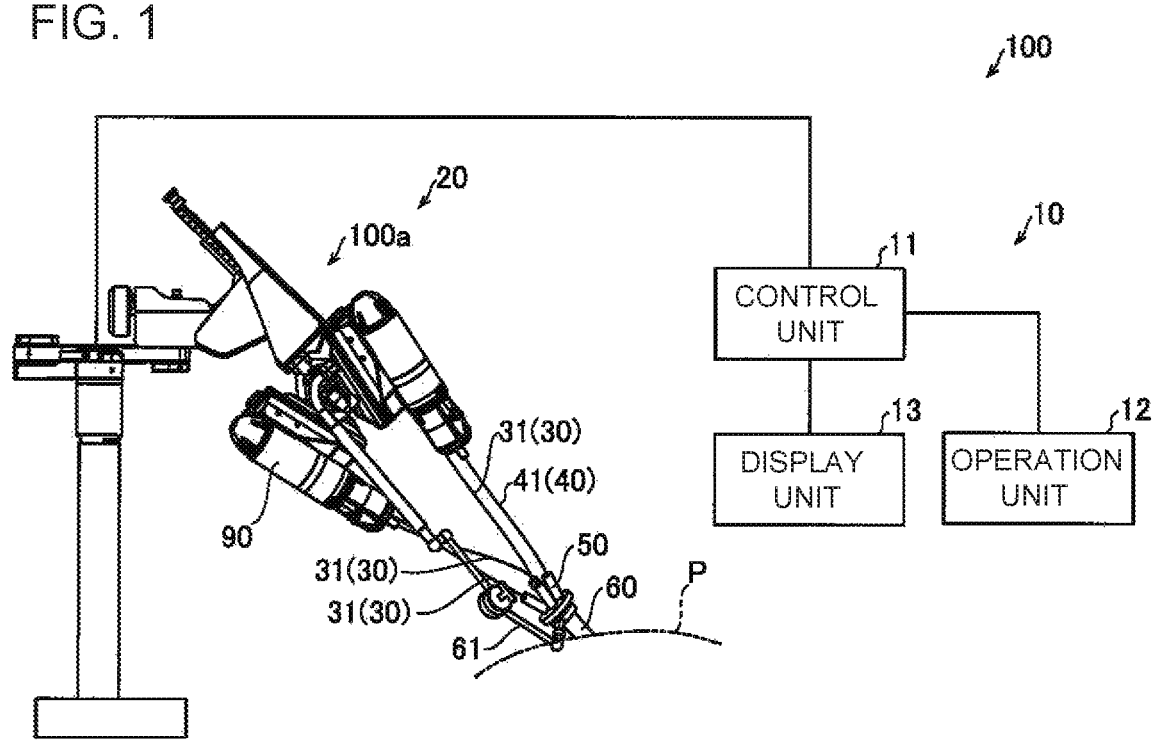
FIG. 1 is a diagram illustrating a schematic view of a robotic surgical system according to an embodiment.

Descriptions are provided hereinbelow for embodiments based on the drawings. In the respective drawings referenced herein, the same constituents are designated by the same reference numerals and duplicate explanation concerning the same constituents is omitted. All of the drawings are provided to illustrate the respective examples only. One or more embodiments will be described with reference to the accompanying drawings.

(Configuration of Robotic Surgical System)

The following describes the configuration of a robotic surgical system 100 according to one or more embodiments with reference to FIGS. 1 to 10.

As illustrated in FIG. 1, the robotic surgical system 100 is a system for performing a surgery on a patient P placed on a medical treatment table. The robotic surgical system 100 includes a remote operation apparatus 10 and a patient-side apparatus 20. The remote operation apparatus 10 is provided to remotely operate medical equipment provided to the patient-side apparatus 20. When an operator, as a surgeon, inputs an action mode command to be executed by the patient-side apparatus 20 to the remote operation apparatus 10, the remote operation apparatus 10 transmits the action mode command to the patient-side apparatus 20 through a control unit 11. Then, in response to the action mode command transmitted from the remote operation apparatus 10, the patient-side apparatus 20 operates medical equipment, such as a surgical instrument 30 or an endoscope 40, attached to a support apparatus 100a. Accordingly, a less invasive endoscopic surgery is performed.

The remote operation apparatus 10 includes the control unit 11, an operation unit 12, and a display unit 13. The control unit 11 controls operation of the patient-side apparatus 20 based on an operation of the operation unit 12 by the operator. The operation unit 12 receives the operation of the patient-side apparatus 20 by the operator. The display unit 13 displays an image of the body cavity of the patient P captured by the endoscope 40 and information related to the surgery.

The patient-side apparatus 20 serves as an interface through which the surgery is performed on the patient P. The patient-side apparatus 20 is arranged beside the medical treatment table on which the patient P is laid. The patient-side apparatus 20 includes one or more surgical instruments 30 and one or more endoscopes 40. The patient-side apparatus 20 also includes one or more guide pipes 50 into each of which the distal end of the corresponding surgical instrument 30 or endoscope 40 is inserted, and a bundling pipe 60 in which the guide pipes 50 are inserted. The number of surgical instruments 30 and the number of endoscopes 40 included in the patient-side apparatus 20 may be any numbers. For example, the patient-side apparatus 20 may include three surgical instruments 30 and one endoscope 40.

Figure 2:
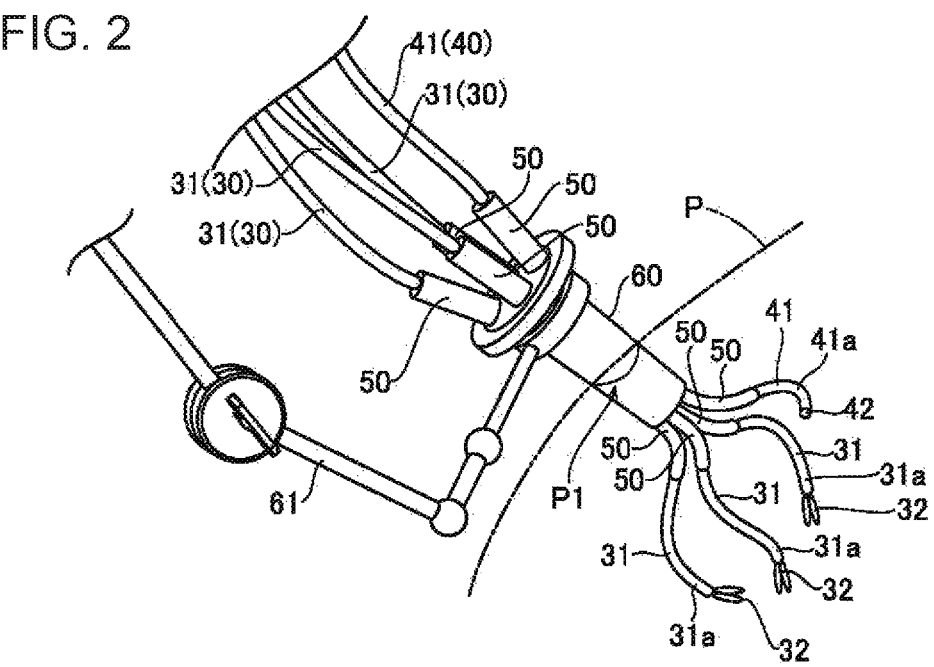
FIG. 2 is a diagram illustrating a view of a surgical instrument, an endoscope, a guide pipe, and a bundling pipe of the robotic surgical system according to an embodiment.

FIG. 2 illustrates an exemplary state of a surgery of the patient P by the patient-side apparatus 20 of the robotic surgical system 100. In FIG. 2, the body surface of the patient P is illustrated with a dashed and double-dotted line, and an incision site P1 formed at the body surface of the patient P is illustrated with a solid line. In FIG. 2, part (distal end) of each of the surgical instrument 30, the endoscope 40, the guide pipes 50, and the bundling pipe 60 is inserted in the body of the patient P through the incision site P1. Such a surgery is, for example, a single port surgery. The robotic surgical system 100 is applicable not only to a surgery in which the surgical instrument 30 and the like are inserted into the body of the patient P through the incision site P1, but also to a natural orifice transluminal endoscopic surgery in which the surgical instrument 30 and so on are inserted into the body of the patient P through a natural orifice such as the oral cavity.

Each surgical instrument 30 and each endoscope 40 include a shaft 31 and a shaft 41, respectively, that are inserted into the guide pipes 50. An end effector 32 for a surgery of the patient P is provided at a distal end 31a of the shaft 31 of the surgical instrument 30. The end effector 32 includes treatment instruments such as grasping forceps, scissors, a hook, a high-frequency knife, a snare wire, a clamp, and a stapler. A camera 42 for image capturing of the body cavity of the patient P is provided at a distal end 41a of the shaft 41 of the endoscope 40. The shaft 31 of the surgical instrument 30 and the shaft 41 of the endoscope 40 are both flexible. In other words, the shaft 31 of the surgical instrument 30 and the shaft 41 of the endoscope 40 can be flexibly bent (curved). When a single port surgery is performed by using surgical instruments and an endoscope including rigid and unbendable shafts, all the rigid shafts of the surgical instruments and the endoscope are inserted into the body of the patient P through the incision site P1. Thus, all the surgical instruments and endoscope need to be arranged adjacent to each other. In contrast, since the flexible shaft 31 and the flexible shaft 41 are bendable, the positions where the surgical instrument 30 and the endoscope 40 are arranged relative to the patient P and the positions where the surgical instrument 30 and the endoscope 40 are supported by the support apparatus 100a are determined more freely than in the case where the rigid and unbendable shafts are used. In addition, since a surgery can be performed on the patient P while bending the shaft 31 and the shaft 41, the end effector 32 and the camera 42 can be more freely moved than in the case where the rigid and unbendable shafts are used. As a result, the end effector 32 and the camera 42 can be easily moved to a surgery site (surgery target site) of the patient P. The shaft 31 is an exemplary "flexible shaft" in the claims.

The guide pipes 50 and the bundling pipe 60 are both flexible. In other words, the guide pipes 50 and the bundling pipe 60 can be flexibly bent (curved). The guide pipes 50 and the bundling pipe 60 are formed of soft plastic such as polypropylene or vinyl chloride. Accordingly, a surgery can be performed on the patient P while the guide pipes 50 and the bundling pipe 60 are bent. The bundling pipe 60 is held by a bundling-pipe holding unit 61. Accordingly, the position and posture of the bundling pipe 60 are fixed.

(Detailed Configuration of Surgical Instrument)

Figure 3:
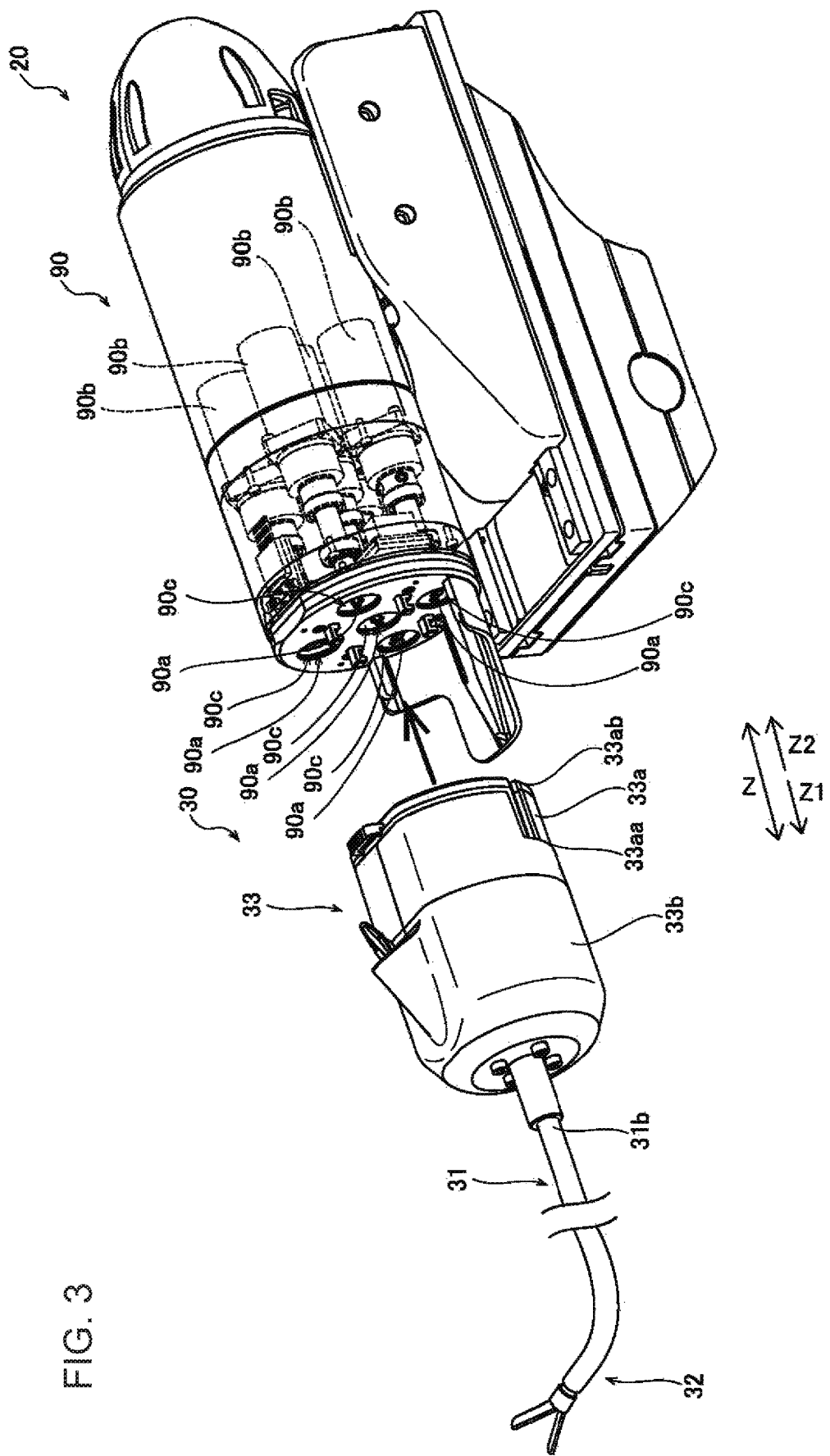
FIG. 3 is a diagram illustrating a perspective view of the surgical instrument and a driving apparatus according to an embodiment.
Figure 4:
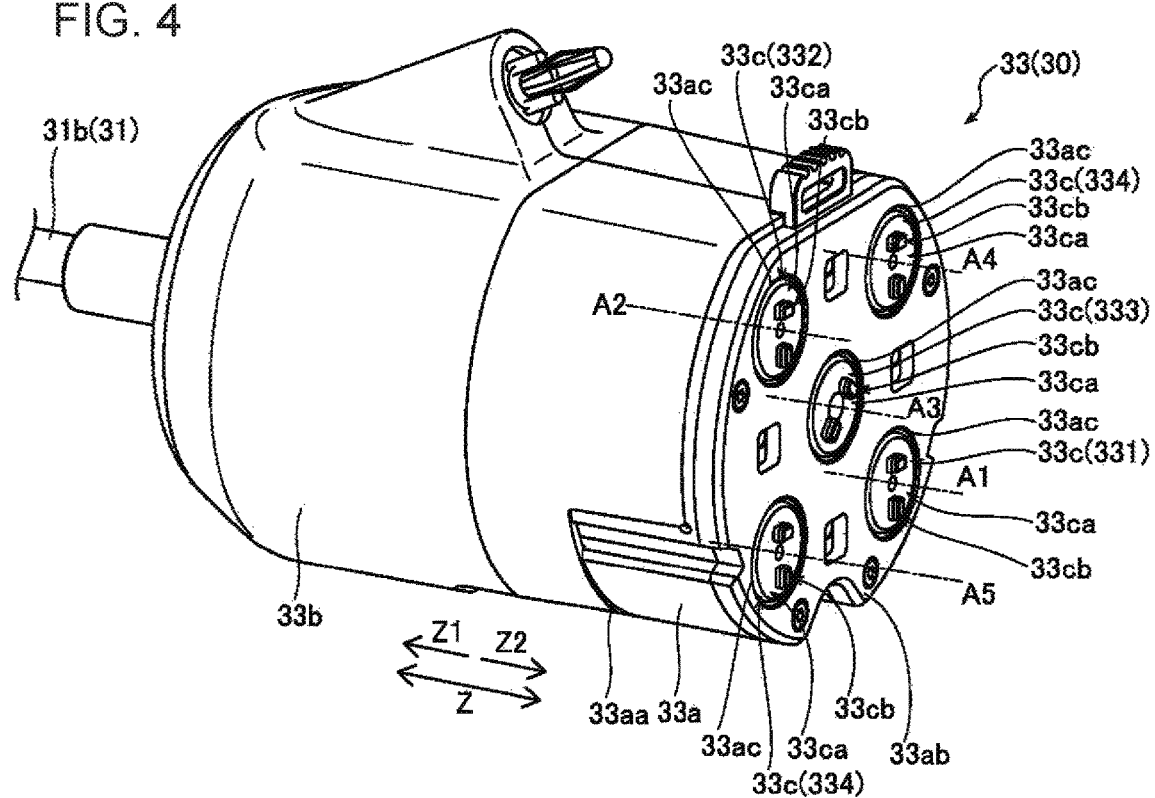
FIG. 4 is a diagram illustrating a perspective view of the surgical instrument according to an embodiment when viewed from a side on which drive is received.

As illustrated in FIGS. 3 and 4, the surgical instrument 30 includes the shaft 31, the end effector 32, and an interface 33. The shaft 31 has an elongated hollow cylindrical shape. The shaft 31 includes the distal end 31a as the distal end, and a proximal end 31b as the proximal end. The shaft 31 is coupled with the end effector 32 on the distal end 31a side. The shaft 31 is also coupled with the interface 33 on the proximal end 31b side.

Figure 5A:
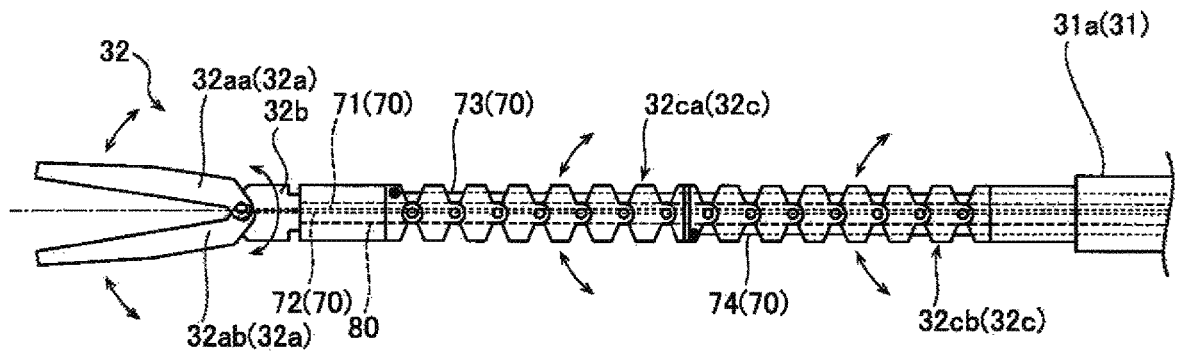
FIG. 5A is a diagram illustrating a view of an end effector of the surgical instrument according to an embodiment.

As illustrated in FIGS. 3 and 5A, the end effector 32 includes an end effector member 32a, a wrist part 32b, and a multi-articulated part 32c (refer to FIG. 5A). The end effector member 32a is provided at the distal end of the end effector 32. The end effector member 32a as a member of grasping forceps includes a first jaw 32aa and a second jaw 32ab. The first jaw 32aa and the second jaw 32ab can be opened and closed independently from each other. The wrist part 32b is coupled with the end effector member 32a on one end side. The wrist part 32b together with the coupled end effector member 32a is provided to be rotatable about a rotational axis. The multi-articulated part 32c is provided in a bendable joint shape. The multi-articulated part 32c includes spinning members arranged in line, and a pin coupling each adjacent spinning members. The multi-articulated part 32c bends as each spinning member rotates about the corresponding pin. The multi-articulated part 32c also includes a first multi-articulated part 32ca and a second multi-articulated part 32cb. The first multi-articulated part 32ca and the second multi-articulated part 32cb are bendable independently from each other.

Figure 5B:
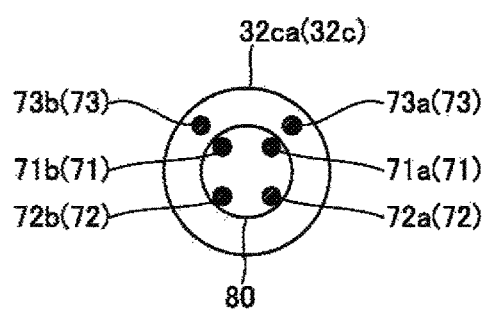
FIG. 5B is a diagram illustrating a schematic cross-sectional view of a first multi-articulated part.
Figure 5C:
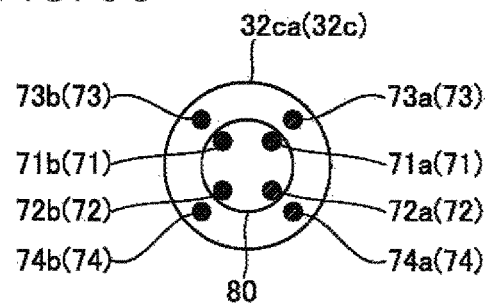
FIG. 5C is a diagram illustrating a schematic cross-sectional view of a second multi-articulated part.

As illustrated in FIGS. 5A to 5C, the surgical instrument 30 includes an elongated element 70 for driving the end effector 32. The elongated element 70 is provided between the end effector 32 and the interface 33 (refer to FIGS. 3 and 4), extending through the hollow shaft 31. The elongated element 70 is coupled with the end effector 32 on one side and wound around and coupled with a driven member 33c of the interface 33, which will be described later, on the other side. In the surgical instrument 30, the end effector 32 coupled with the elongated element 70 is driven as the elongated element 70 is pulled and fed out through rotation of the driven member 33c as a rotation member. The elongated element 70 may be, for example, a wire or a cable.

The elongated element 70 includes an elongated element 71 for opening and closing the first jaw 32aa of the end effector member 32a, an elongated element 72 for opening and closing the second jaw 32ab of the end effector member 32a, an elongated element 73 for bending the first multi-articulated part 32ca of the multi-articulated part 32c, and an elongated element 74 for bending the second multi-articulated part 32cb of the multi-articulated part 32c.

The elongated element 71 includes a first part 71a and a second part 71b between the first jaw 32aa of the end effector 32 and the driven member 33c (331) of the interface 33. The first part 71a and the second part 71b move in directions opposite to each other in opening and closing operation of the first jaw 32aa by the driven member 33c (331). The first part 71a and the second part 71b may be formed of two elongated elements 71 or one elongated element 71 including a folding part. The first part 71a and the second part 71*b* are each coupled with the first jaw 32*aa* of the end effector 32 on one side and wound around and coupled with the driven member 33*c* (331) of the interface 33 on the other side.

Similarly, the elongated element 72 includes a first part 72*a* and a second part 72*b* between the second jaw 32*ab* of the end effector 32 and the driven member 33*c* (332) of the interface 33. The first part 72*a* and the second part 72*b* move in directions opposite to each other in opening and closing operation of the second jaw 32*ab* by the driven member 33*c* (332). The first part 72*a* and the second part 72*b* may be formed of two elongated elements 72 or one elongated element 72 including a folding part. The first part 72*a* and the second part 72*b* are each coupled with the second jaw 32*ab* of the end effector 32 on one side and wound around and coupled with on the other side the driven member 33*c* (332) of the interface 33.

The elongated element 73 includes a first part 73*a* and a second part 73*b* between the first multi-articulated part 32*ca* of the end effector 32 and the driven member 33*c* (334) of the interface 33. The first part 73*a* and the second part 73*b* move in directions opposite to each other in bending operation of the first multi-articulated part 32*ca* by the driven member 33*c* (334). The first part 73*a* and the second part 73*b* may be formed of two elongated elements 73 or one elongated element 73 including a folding part. The first part 73*a* and the second part 73*b* are each coupled with the first multi-articulated part 32*ca* of the end effector 32 on one side and wound around and coupled with the driven member 33*c* (334) of the interface 33 on the other side.

Similarly, the elongated element 74 includes a first part 74*a* and a second part 74*b* between the second multi-articulated part 32*cb* of the end effector 32 and the driven member 33*c* (335) of the interface 33. The first part 74*a* and the second part 74*b* move in directions opposite to each other in bending operation of the second multi-articulated part 32*cb* by the driven member 33*c* (335). The first part 74*a* and the second part 74*b* may be formed of two elongated elements 74 or one elongated element 74 including a folding part. The first part 74*a* and the second part 74*b* are each coupled with the second multi-articulated part 32*cb* of the end effector 32 on one side and wound around and coupled with the driven member 33*c* (335) of the interface 33 on the other side. To facilitate understanding, FIG. 5A illustrates only some (the first parts 71*a* to 74*a* or the second parts 71*b* to 74*b*) of the elongated elements 71 to 74.

The surgical instrument 30 includes a torque transferring tube 80 for driving the wrist part 32*b* of the end effector 32. The torque transferring tube 80 is provided between the wrist part 32*b* of the end effector 32 and the interface 33, extending through the hollow shaft 31. The torque transferring tube 80 includes a first end as a one side end, and a second end as the other side end, and is coupled with the wrist part 32*b* of the end effector 32 at the first end and with the interface 33 at the second end. In the surgical instrument 30, the wrist part 32*b* coupled with the torque transferring tube 80 is rolled with respect to the shaft 31*b* (e.g. is rotated about the axis of the distal end of the shaft 31) as the torque transferring tube 80 is rotated by the driven member 33*c* (333) of the interface 33, which will be described later. In this case, the first and second jaws 32*ca* and 32*cb* of the end effector member 32*a* coupled with the wrist part 32*b* are rotated together with the wrist part 32*b*. The torque transferring tube 80 is flexible. In other words, the torque transferring tube 80 can be flexibly bent (curved). The torque transferring tube 80 is an exemplary "torque transferring member" in the claims.

The torque transferring tube 80 is coupled with the wrist part 32*b* of the end effector 32, extending through the hollow multi-articulated part 32*c*. The elongated elements 71 and 72 for the end effector member 32*a* of the end effector 32 described above extend through the hollow torque transferring tube 80. The elongated elements 73 and 74 for the multi-articulated part 32*c* of the end effector 32 described above extend outside the hollow torque transferring tube 80. In other words, the elongated elements 71 and 72 for the end effector member 32*a* of the end effector 32 are separated from the elongated elements 73 and 74 for the multi-articulated part 32*c* of the end effector 32 through the torque transferring tube 80.

As illustrated in FIGS. 3 and 4, the interface 33 includes a base 33*a*, a cover 33*b*, and a plurality (five) of driven members 33*c*. The base 33*a* includes a first surface 33*aa* as a surface on one side, and a second surface 33*ab* as a surface on the other side. The first surface 33*aa* and the second surface 33*ab* are orthogonal to a rotational axis A1 (A2 to A5) of each driven member 33*c*. The base 33*a* includes through-holes 33*ac* penetrating through the first surface 33*aa* and the second surface 33*ab* in a direction (Z direction) along the rotational axis A1 (A2 to A5) of the driven member 33*c*. The cover 33*b* is provided to cover the base 33*a* from the first surface 33*aa* side of the base 33*a*. The driven member 33*c* is provided to be rotatable about the rotational axis A1 (A2 to A5) in the corresponding through-hole 33*ac* of the base 33*a*. The driven member 33*c* has a surface 33*ca* that receives drive on the second surface 33*ab* side (Z2 direction side) of the base 33*a*. The surface 33*ca* of each of driven member 33*c* is provided at the second surface 33*ab* of the base 33*a*. Accordingly, the positions of the surfaces 33*ca* of the respective driven members 33*c*, which receive drive, are aligned with each other. This leads to simplification of the configuration (structure) of the surgical instrument 30.

The second surface 33*ab* side (the Z2 direction side) of the base 33*a* is mounted on a driving apparatus 90 as the surgical instrument 30 moves in the direction (Z1 direction) along the rotational axis A1 (A2 to A5) of the driven member 33*c*. The driving apparatus 90 generates drive power for driving the end effector 32. When the surgical instrument 30 is mounted on the driving apparatus 90, the driven member 33*c* is rotated about the rotational axis A1 (A2 to A5) by a driving member 90*c* of the driving apparatus 90. Accordingly, the surgical instrument 30 can be easily mounted on the driving apparatus 90, and the driven member 33*c* of the surgical instrument 30 mounted on the driving member 90*c* of the driving apparatus 90 can be easily rotated.

The driven member 33*c* includes a first engagement portion 33*cb* at the surface 33*ca* provided on the second surface 33*cb* side of the base 33*a* to receive drive. The first engagement portion 33*cb* is engaged with a second engagement portion 90*a* provided to the driving member 90*c* of the driving apparatus 90 and rotated. Accordingly, rotational force generated by the driving apparatus 90 can be reliably transferred to the driven member 33*c*, and thus the driven member 33*c* can be reliably rotated. The first engagement portion 33*cb* and the second engagement portion 90*a* have, for example, concave and convex shapes to be engaged with each other. In this case, the first engagement portion 33*cb* may be, for example, a convex portion protruding toward the Z2 direction side, and the second engagement portion 90*a* may be, for example, a concave portion recessed toward the Z2 direction side. The driving apparatus 90 includes a driving motor 90*b* that rotates the driving member 90*c* including the second engagement portion 90*a*. The driving motor 90b is provided for each driving member 90c including the second engagement portion 90a. Thus, the driving members 90c are rotatable independently from each other. Similarly, the driven members 33c are rotatable independently from each other. The surgical instrument 30 is detachably attached to the driving apparatus 90.

(Detailed Configuration of Interface)

Figure 6:
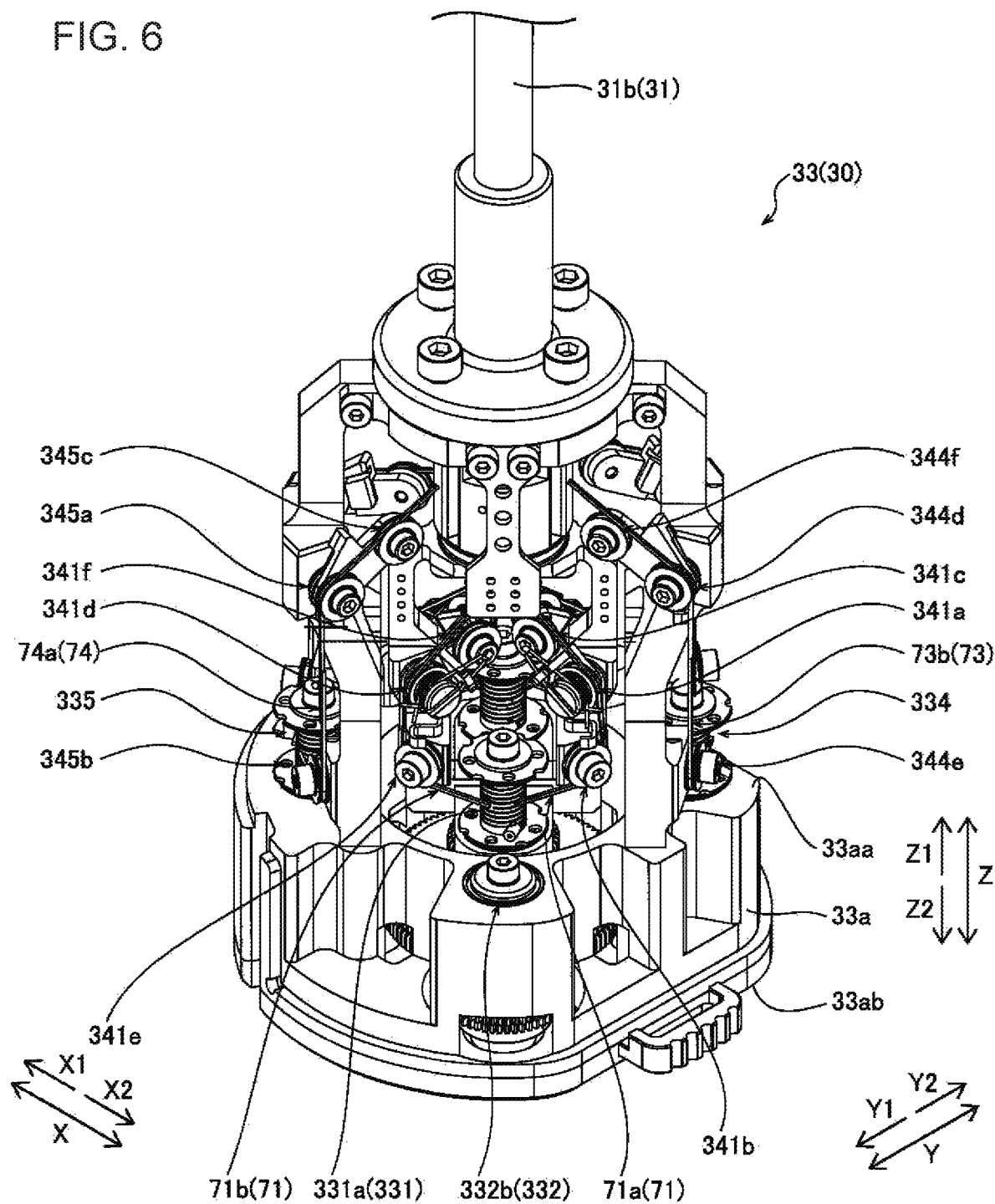
FIG. 6 is a diagram illustrating a view a perspective view of an interface of the surgical instrument according to an embodiment.
Figure 7:
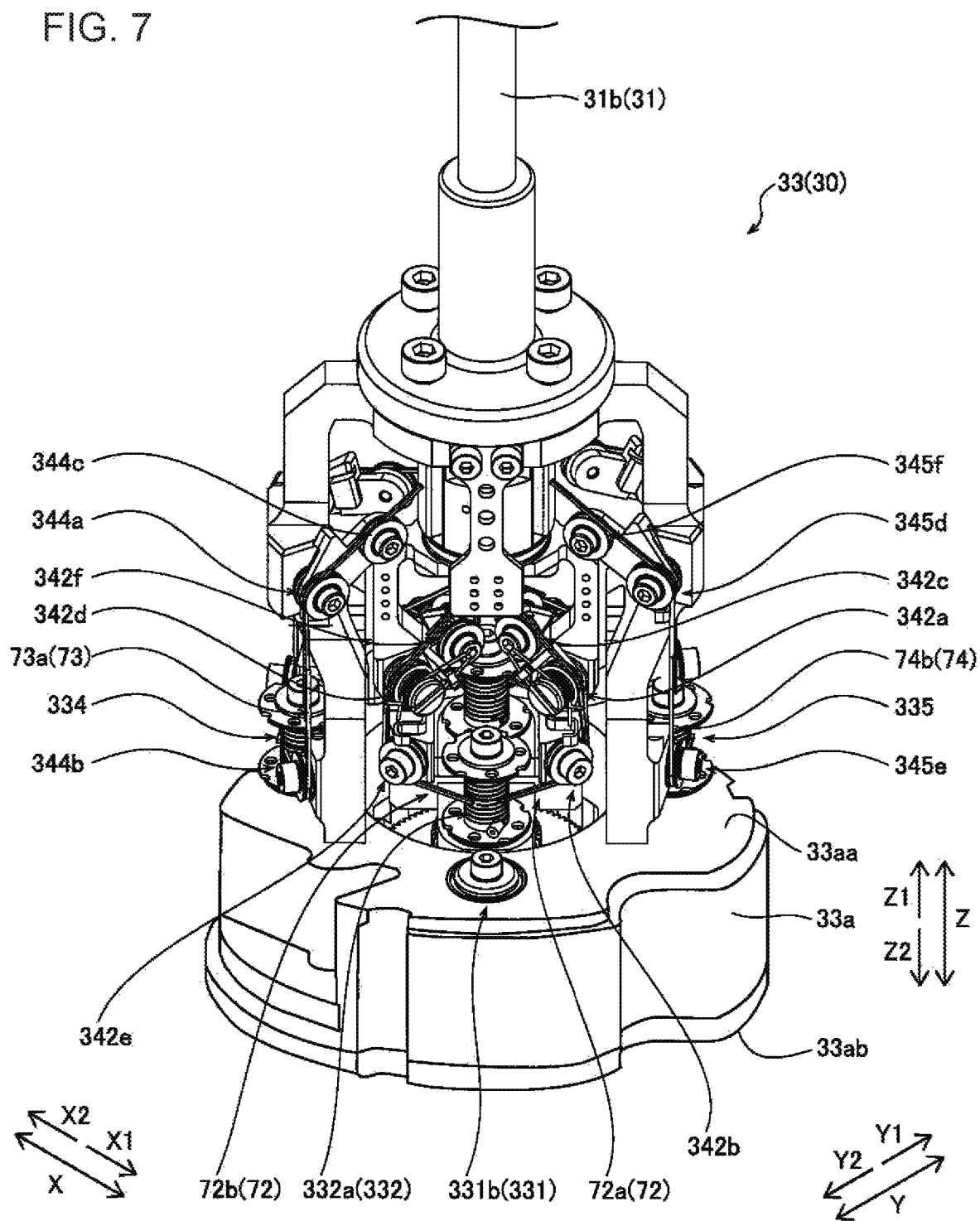
FIG. 7 is a diagram illustrating a perspective view of the interface of the surgical instrument according to an embodiment when viewed from a side opposite to that of FIG. 6.

As illustrated in FIGS. 6 and 7, each driven member 33c of the interface 33 includes a driven member 331 for opening and closing the first jaw 32aa of the end effector 32, a driven member 332 for opening and closing the second jaw 32ab of the end effector 32, a driven member 333 for rotating the wrist part 32b of the end effector 32, a driven member 334 for bending the first multi-articulated part 32ca of the end effector 32, and a driven member 335 for bending the second multi-articulated part 32cb of the end effector 32.

<Configuration for Opening and Closing First Jaw>

As illustrated in FIG. 6, the first part 71a and the second part 71b of the elongated element 71 guided through and drawn from the shaft 31 are wound around the driven member 331. In addition, a first guide pulley 341a and a second guide pulley 341b that guide the first part 71a of the elongated element 71 are provided to the interface 33. The first guide pulley 341a is arranged between the proximal end 31b of the shaft 31 and the driven member 331 and provided to guide the first part 71a of the elongated element 71 drawn from the proximal end 31b of the shaft 31 toward the second guide pulley 341b in the direction (Z direction) along the rotational axis A1 (A6) of the driven member 331. The second guide pulley 341b is arranged between the first guide pulley 341a and the driven member 331 and provided to guide the first part 71a of the elongated element 71 guided by the first guide pulley 341a toward the driven member 331 in a direction intersecting the rotational axis A1 (A6) of the driven member 331. With this configuration, the driven member 331 can be arranged such that the axis thereof is aligned with a direction along the longitudinal direction (Z direction) of the surgical instrument 30 and thus can receive drive of the driving apparatus 90 from the second surface 33ab side of the base 33a, and accordingly, the surgical instrument 30 can be easily mounted on the driving apparatus 90 by moving the surgical instrument 30 in the direction along the longitudinal direction of the surgical instrument 30. In addition, the first part 71a of the elongated element 71 can be easily wound around the driven member 331 while the driven member 331 around which the first part 71a of the elongated element 71 is wound is provided at a position separated from the proximal end 31b of the shaft 31 in a direction intersecting the axial direction (Z direction) of the shaft 31 at the proximal end 31b.

In addition, the interface 33 is provided with a tension pulley 341c that is arranged between the proximal end 31b of the shaft 31 and the first guide pulley 341a and biases the first part 71a of the elongated element 71. Accordingly, the tension of the first part 71a of the elongated element 71 can be adjusted by the tension pulley 341c, and thus the occurrence of slack to the first part 71a of the elongated element 71 can be reduced when the direction in which the first part 71a of the elongated element 71 extends is changed by the first guide pulley 341a and the second guide pulley 341b. In addition, since the tension pulley 341c is provided on the path of the first part 71a of the elongated element 71 from the proximal end 31b of the shaft 31 to the driven member 331, no large space is needed to provide the tension pulley 341c, which leads to downsizing of the surgical instrument 30.

The tension pulley 341c is movable in the circumferential direction of a circle centered at the first guide pulley 341a. Accordingly, when force that the tension pulley 341c receives from the first part 71a of the elongated element 71 is larger than the biasing force of the tension pulley 341c because the tension of the first part 71a of the elongated element 71 is large, the tension pulley 341c can be moved in one of directions along the circumferential direction as if the tension pulley 341c were pressed by the first part 71a of the elongated element 71. As a result, excessively large biasing force can be prevented from being applied to the elongated element 71. When force that the tension pulley 341c receives from the first part 71a of the elongated element 71 is smaller than the biasing force of the tension pulley 341c because the tension of the first part 71a of the elongated element 71 is small, the tension pulley 341c can be moved in the other direction along the circumferential direction as if the tension pulley 341c pressed the first part 71a of the elongated element 71. As a result, excessively small biasing force can be prevented from being applied to the elongated element 71. With these results, tension applied to the first part 71a of the elongated element 71 can be stabilized. The tension pulley 341c receives biasing force by an elastic member such as a line spring and biases the first part 71a of the elongated element 71 in the circumferential direction of a circle centered at the first guide pulley 341a.

The tension pulley 341c, the first guide pulley 341a, and the second guide pulley 341b are arranged in this order from the proximal end 31b of the shaft 31 side toward the driven member 331. The tension pulley 341c is arranged to bias a straight portion of the first part 71a of the elongated element 71 between the proximal end 31b of the shaft 31 and the first guide pulley 341a. The first guide pulley 341a is arranged such that the first part 71a of the elongated element 71 drawn from the proximal end 31b of the shaft 31 through the tension pulley 341c is guided toward the second guide pulley 341b by being bent approximately at an angle equal to or larger than 90° and smaller than 180°. In addition, the first guide pulley 341a is provided at a position separated from the proximal end 31b of the shaft 31 in the direction intersecting the axial direction (Z direction) of the shaft 31 and guides, in a direction along the rotational axis A1 (A6) of the driven member 331, the first part 71a of the elongated element 71 pulled out from the proximal end 31b of the shaft 31 in the direction intersecting the axial direction of the shaft 31. The second guide pulley 341b is arranged such that the first part 71a of the elongated element 71 guided from the first guide pulley 341a is guided toward the driven member 331 by being bent at an angle of approximately 90°. Accordingly, the first part 71a of the elongated element 71 can be guided at an angle with which the first part 71a can be easily wound around the driven member 331.

The interface 33 is also provided with, for the second part 71b of the elongated element 71, a configuration similar to that of the first part 71a of the elongated element 71 described above. Specifically, the interface 33 is provided with a third guide pulley 341d and a fourth guide pulley 341e that guide the second part 71b of the elongated element 71. The third guide pulley 341d is arranged between the proximal end 31b of the shaft 31 and the driven member 331 and provided to guide the second part 71b of the elongated element 71 drawn from the proximal end 31b of the shaft 31 toward the fourth guide pulley 341e in the direction (Z direction) along the rotational axis A1 (A6) of the driven member 331. The fourth guide pulley 341e is arranged between the third guide pulley 341d and the driven member 331 and provided to guide the second part 71b of the elongated element 71 guided by the third guide pulley 341d toward the driven member 331 in the direction intersecting the rotational axis A1 (A6) of the driven member 331. With this configuration, the driven member 331 can be arranged such that the axis thereof is aligned with the direction along the longitudinal direction (Z direction) of the surgical instrument 30 and thus can receive drive of the driving apparatus 90 from the second surface 33ab side of the base 33a, and accordingly, the surgical instrument 30 can be easily mounted on the driving apparatus 90 by moving the surgical instrument 30 in the direction along the longitudinal direction of the surgical instrument 30. In addition, the second part 71b of the elongated element 71 can be easily wound around the driven member 331 while the driven member 331 around which the second part 71b of the elongated element 71 is wound is provided at a position separated from the proximal end 31b of the shaft 31 in the direction intersecting the axial direction (Z direction) of the shaft 31 at the proximal end 31b.

The interface 33 is also provided with a tension pulley 341f that is arranged between the proximal end 31b of the shaft 31 and the third guide pulley 341d and biases the second part 71b of the elongated element 71. Accordingly, the tension of the second part 71b of the elongated element 71 can be adjusted by the tension pulley 341f, and thus the occurrence of slack to the second part 71b of the elongated element 71 can be reduced when the direction in which the second part 71b of the elongated element 71 extends is changed by the third guide pulley 341d and the fourth guide pulley 341e. In addition, since the tension pulley 341f is provided on the path of the second part 71b of the elongated element 71 from the proximal end 31b of the shaft 31 to the driven member 331, no large space is needed to provide the tension pulley 341f, which leads to downsizing of the surgical instrument 30.

The tension pulley 341f is movable in the circumferential direction of a circle centered at the third guide pulley 341d. Accordingly, when force that the tension pulley 341f receives from the second part 71b of the elongated element 71 is larger than the biasing force of the tension pulley 341f because the tension of the second part 71b of the elongated element 71 is large, the tension pulley 341f can be moved in one of directions along the circumferential direction as if the tension pulley 341f were pressed from the second part 71b of the elongated element 71. As a result, excessively large biasing force can be prevented from being applied to the elongated element 71. When force that the tension pulley 341f receives from the second part 71b of the elongated element 71 is smaller than the biasing force of the tension pulley 341f because the tension of the second part 71b of the elongated element 71 is small, the tension pulley 341f can be moved in the other direction along the circumferential direction as if the tension pulley 341f pressed the second part 71b of the elongated element 71. As a result, excessively small biasing force can be prevented from being applied to the elongated element 71. With these results, tension applied to the second part 71b of the elongated element 71 can be stabilized. The tension pulley 341f receives biasing force by an elastic member such as a line spring and biases the second part 71b of the elongated element 71 in the circumferential direction of a circle centered at the third guide pulley 341d.

The tension pulley 341f, the third guide pulley 341d, and the fourth guide pulley 341e are arranged in this order from the proximal end 31b of the shaft 31 side toward the driven member 331. The tension pulley 341f is arranged to bias a straight portion of the second part 71b of the elongated element 71 between the proximal end 31b of the shaft 31 and the third guide pulley 341d. The third guide pulley 341d is arranged such that the second part 71b of the elongated element 71 drawn from the proximal end 31b of the shaft 31 through the tension pulley 341f is guided toward the fourth guide pulley 341e by being bent approximately at an angle equal to or larger than 90° and smaller than 180°. In addition, the third guide pulley 341d is provided at a position separated from the proximal end 31b of the shaft 31 in the direction intersecting the axial direction (Z direction) of the shaft 31 and guides, in the direction along the rotational axis A1 (A6) of the driven member 331, the second part 71b of the elongated element 71 pulled out from the proximal end 31b of the shaft 31 in the direction intersecting the axial direction of the shaft 31. The fourth guide pulley 341e is arranged such that the second part 71b of the elongated element 71 guided from the third guide pulley 341d is guided toward the driven member 331 by being bent at an angle of approximately 90°. Accordingly, the second part 71b of the elongated element 71 can be guided at an angle with which the second part 71b can be easily wound around the driven member 331.

Each of the first guide pulley 341a, the second guide pulley 341b, and the tension pulley 341c and the corresponding one of the third guide pulley 341d, the fourth guide pulley 341e, and the tension pulley 341f are provided at positions substantially symmetric to each other with the driven member 331 interposed therebetween.

Figure 8:
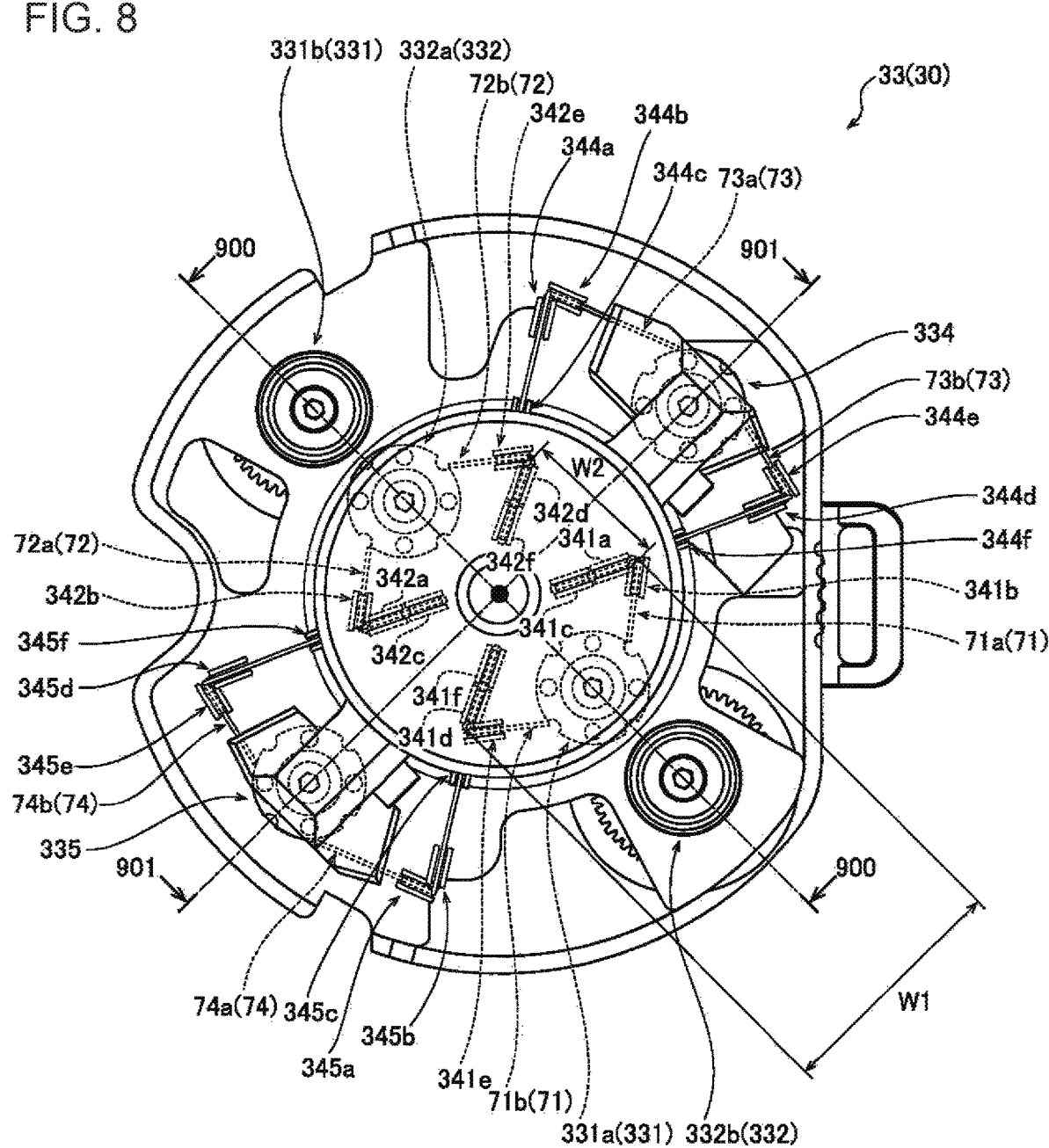
FIG. 8 is a diagram illustrating a view of the interface of the surgical instrument according to an embodiment when viewed from a Z1 direction side.
Figure 8:
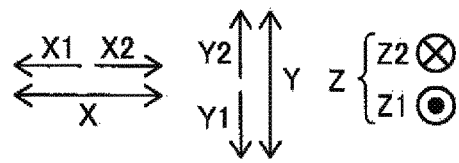
Figure 9:
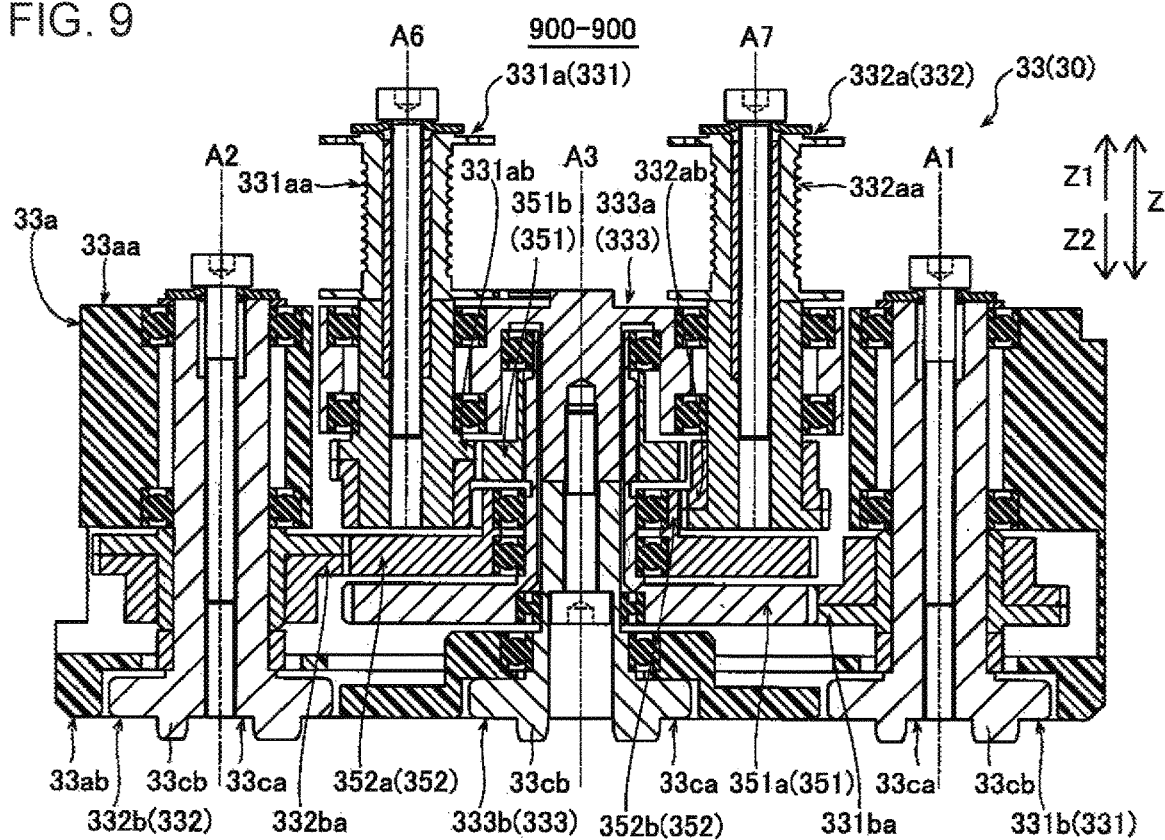
FIG. 9 is a diagram illustrating a schematic cross-sectional view along line 900-900 in FIG. 8.

As illustrated in FIGS. 8 and 9, the driven member 331 includes a winding member 331a around which the first part 71a and the second part 71b of the elongated element 71 is wound, and a drive receiving member 331b that receives drive of the driving apparatus 90 for rotating the winding member 331a. The winding member 331a is a rotation member rotatable about the rotational axis A6 orthogonal to the second surface 33ab of the base 33a. The winding member 331a includes a winding part 331aa and a gear part 331ab. The winding part 331aa protrudes from the first surface 33aa of the base 33a so that the first part 71a and the second part 71b of the elongated element 71 guided through the shaft 31 are wound around the winding part 331aa. The gear part 331ab is provided between the first surface 33aa of the base 33a and the second surface 33ab. The drive receiving member 331b is a rotation member facing the second surface 33ab of the base 33a and rotatable about the rotational axis A1 orthogonal to the second surface 33ab of the base 33a. The drive receiving member 331b includes the above-described surface 33ca that receives drive and the first engagement portion 33cb. The drive receiving member 331b also includes a gear part 331ba. The winding member 331a and the drive receiving member 331b are not coaxially arranged.

The winding member 331a and the drive receiving member 331b, which are not coaxially arranged are connected with each other through a gear part 351 as a drive transferring member between the winding member 331a and the drive receiving member 331b. Accordingly, drive power received by the drive receiving member 331b can be reliably transferred to the winding member 331a through the gear part 351. The gear part 351 includes a first gear part 351a engaged with the gear part 331ba of the drive receiving member 331b, and a second gear part 351b engaged with the gear part 331ab of the winding member 331a. The first gear part 351a and the second gear part 351b of the gear part 351 are coupled with each other to be integrally rotated. In the surgical instrument 30, the first gear part 351a of the gear part 351 engaged with the gear part 331ba of the drive receiving member 331b is rotated as the drive receiving member 331*b* of the driven member 331 is rotated by the driving apparatus 90. As a result, the second gear part 351*b* coupled with the first gear part 351*a* of the gear part 351 is rotated, and the winding member 331*a* of the driven member 331 engaged with the second gear part 351*b* of the gear part 351 is rotated. Accordingly, the first part 71*a* and the second part 71*b* of the elongated element 71 wound around the winding member 331*a* of the driven member 331 are operated, and the first jaw 32*aa* of the end effector 32 coupled with the first part 71*a* and the second part 71*b* of the elongated element 71 are opened and closed. The gear part 351 is an exemplary "gear member" in the claims.

The gear part 351 is arranged such that the rotational axis A3 of the driven member 333 for rotating the wrist part 32*b* of the end effector 32 is coaxial with the rotational axis. Accordingly, the gear part 351 and the driven member 333 are collectively arranged at one place, which leads to downsizing of the surgical instrument 30. Rotation of the gear part 351 is separated from the driven member 333 through, for example, a bearing. The gear part 351 is separated from the driven member 333 so that the driven member 333 does not rotate when the gear part 351 rotates.

Accordingly, independence of drive of the driven member 331 can be maintained while the surgical instrument 30 is downsized.

<Configuration for Opening and Closing Second Jaw>

A configuration for opening and closing the second jaw 32*ab* of the end effector 32 is substantially same as the above-described configuration for opening and closing the first jaw 32*aa* of the end effector 32. Specifically, as illustrated in FIG. 7, the first part 72*a* and the second part 72*b* of the elongated element 72 guided through the shaft 31 are wound around the driven member 332. The interface 33 is also provided with a first guide pulley 342*a* and a second guide pulley 342*b* that guide the first part 72*a* of the elongated element 72. The first guide pulley 342*a* is arranged between the proximal end 31*b* of the shaft 31 and the driven member 332 and provided to guide the first part 72*a* of the elongated element 72 drawn from the proximal end 31*b* of the shaft 31 toward the second guide pulley 342*b* in the direction (Z direction) along the rotational axis A2 (A7) of the driven member 332. The second guide pulley 342*b* is arranged between the first guide pulley 342*a* and the driven member 332 and provided to guide the first part 72*a* of the elongated element 72 guided by the first guide pulley 342*a* toward the driven member 332 in a direction intersecting the rotational axis A2 (A7) of the driven member 332. With this configuration, the driven member 332 can be arranged such that the axis thereof is aligned with the direction along the longitudinal direction (Z direction) of the surgical instrument 30 and thus can receive drive of the driving apparatus 90 from the second surface 33*ab* side of the base 33*a*, and accordingly, the surgical instrument 30 can be easily mounted on the driving apparatus 90 by moving the surgical instrument 30 in the direction along the longitudinal direction of the surgical instrument 30. In addition, the first part 72*a* of the elongated element 72 can be easily wound around the driven member 332 while the driven member 332 around which the first part 72*a* of the elongated element 72 is wound is provided at a position separated from the proximal end 31*b* of the shaft 31 in the direction intersecting the axial direction (Z direction) of the shaft 31 at the proximal end 31*b*.

The interface 33 is also provided with a tension pulley 342*c* that is arranged between the proximal end 31*b* of the shaft 31 and the first guide pulley 342*a* and biases the first part 72*a* of the elongated element 72. Accordingly, the tension of the first part 72*a* of the elongated element 72 can be adjusted by the tension pulley 342*c*, and thus the occurrence of slack to the first part 72*a* of the elongated element 72 can be reduced when the direction in which the first part 72*a* of the elongated element 72 extends is changed by the first guide pulley 342*a* and the second guide pulley 342*b*. In addition, since the tension pulley 342*c* is provided on the path of the first part 72*a* of the elongated element 72 from the proximal end 31*b* of the shaft 31 to the driven member 332, no large space is needed to provide the tension pulley 342*c*, which leads to downsizing of the surgical instrument 30.

The tension pulley 342*c* is movable in the circumferential direction of a circle centered at the first guide pulley 342*a*. Accordingly, when force that the tension pulley 342*c* receives from the first part 72*a* of the elongated element 72 is larger than the biasing force of the tension pulley 342*c* because the tension of the first part 72*a* of the elongated element 72 is large, the tension pulley 342*c* can be moved in one of directions along the circumferential direction as if the tension pulley 342*c* were pressed from the first part 72*a* of the elongated element 72. As a result, excessively large biasing force can be prevented from being applied to the elongated element 72. When force that the tension pulley 342*c* receives from the first part 72*a* of the elongated element 72 is smaller than the biasing force of the tension pulley 342*c* because the tension of the first part 72*a* of the elongated element 72 is small, the tension pulley 342*c* can be moved in the other direction along the circumferential direction as if the tension pulley 342*c* pressed the first part 72*a* of the elongated element 72. As a result, excessively small biasing force can be prevented from being applied to the elongated element 72. With these results, tension applied to the first part 72*a* of the elongated element 72 can be stabilized. The tension pulley 342*c* receives biasing force by an elastic member such as a line spring and biases the first part 72*a* of the elongated element 72 in the circumferential direction of a circle centered at the first guide pulley 342*a*.

The tension pulley 342*c*, the first guide pulley 342*a*, and the second guide pulley 342*b* are arranged in this order from the proximal end 31*b* of the shaft 31 side toward the driven member 332. The tension pulley 342*c* is arranged to bias a straight portion of the first part 72*a* of the elongated element 72 between the proximal end 31*b* of the shaft 31 and the first guide pulley 342*a*. The first guide pulley 342*a* is arranged such that the first part 72*a* of the elongated element 72 drawn from the proximal end 31*b* of the shaft 31 through the tension pulley 342*c* is guided toward the second guide pulley 342*b* by being bent approximately at an angle equal to or larger than 90° and smaller than 180°. In addition, the first guide pulley 342*a* is provided at a position separated from the proximal end 31*b* of the shaft 31 in the direction intersecting the axial direction (Z direction) of the shaft 31 and guides, in a direction along the rotational axis A2 (A7) of the driven member 332, the first part 72*a* of the elongated element 72 pulled out from the proximal end 31*b* of the shaft 31 in the direction intersecting the axial direction of the shaft 31. The second guide pulley 342*b* is arranged such that the first part 72*a* of the elongated element 72 guided from the first guide pulley 342*a* is guided toward the driven member 332 by being bent at an angle of approximately 90°. Accordingly, the first part 72*a* of the elongated element 72 can be guided at an angle with which the first part 72*a* can be easily wound around the driven member 332.

The interface 33 is also provided with, for the second part 72*b* of the elongated element 72, a configuration similar to that of the first part 72*a* of the elongated element 72 described above. Specifically, the interface 33 is provided with a third guide pulley 342*d* and a fourth guide pulley 342*e* that guide the second part 72*b* of the elongated element 72. The third guide pulley 342*d* is arranged between the proximal end 31*b* of the shaft 31 and the driven member 332 and provided to guide the second part 72*b* of the elongated element 72 drawn from the proximal end 31*b* of the shaft 31 toward the fourth guide pulley 342*e* in the direction (Z direction) along the rotational axis A2 (A7) of the driven member 332. The fourth guide pulley 342*e* is arranged between the third guide pulley 342*d* and the driven member 332 and provided to guide the second part 72*b* of the elongated element 72 guided by the third guide pulley 342*d* toward the driven member 332 in the direction intersecting the rotational axis A2 (A7) of the driven member 332. With this configuration, the driven member 332 can be arranged such that the axis thereof is aligned with the direction along the longitudinal direction (Z direction) of the surgical instrument 30 and thus can receive drive of the driving apparatus 90 from the second surface 33*ab* side of the base 33*a*, and accordingly, the surgical instrument 30 can be easily mounted on the driving apparatus 90 by moving the surgical instrument 30 in the direction along the longitudinal direction of the surgical instrument 30. In addition, the second part 72*b* of the elongated element 72 can be easily wound around the driven member 332 while the driven member 332 around which the second part 72*b* of the elongated element 72 is wound is provided at a position separated from the proximal end 31*b* of the shaft 31 in the direction intersecting the axial direction (Z direction) of the shaft 31 at the proximal end 31*b*.

The interface 33 is also provided with a tension pulley 342*f* that is arranged between the proximal end 31*b* of the shaft 31 and the third guide pulley 342*d* and biases the second part 72*b* of the elongated element 72. Accordingly, the tension of the second part 72*b* of the elongated element 72 can be adjusted by the tension pulley 342*f*, and thus the occurrence of slack to the second part 72*b* of the elongated element 72 can be reduced when the direction in which the second part 72*b* of the elongated element 72 extends is changed by the third guide pulley 342*d* and the fourth guide pulley 342*e*. In addition, since the tension pulley 342*f* is provided on the path of the second part 72*b* of the elongated element 72 from the proximal end 31*b* of the shaft 31 to the driven member 332, no large space is needed to provide the tension pulley 342*f*, which leads to downsizing of the surgical instrument 30.

The tension pulley 342*f* is movable in the circumferential direction of a circle centered at the third guide pulley 342*d*. Accordingly, when force that the tension pulley 342*f* receives from the second part 72*b* of the elongated element 72 is larger than the biasing force of the tension pulley 342*f* because the tension of the second part 72*b* of the elongated element 72 is large, the tension pulley 342*f* can be moved in one of directions along the circumferential direction as if the tension pulley 342*f* were pressed from the second part 72*b* of the elongated element 72. As a result, excessively large biasing force can be prevented from being applied to the elongated element 72. When force that the tension pulley 342*f* receives from the second part 72*b* of the elongated element 72 is smaller than the biasing force of the tension pulley 342*f* because the tension of the second part 72*b* of the elongated element 72 is small, the tension pulley 342*f* can be moved in the other direction along the circumferential direction as if the tension pulley 342*f* pressed the second part 72*b* of the elongated element 72. As a result, excessively small biasing force can be prevented from being applied to the elongated element 72. With these results, tension applied to the second part 72*b* of the elongated element 72 can be stabilized. The tension pulley 342*f* receives biasing force by an elastic member such as a line spring and biases the second part 72*b* of the elongated element 72 in the circumferential direction of a circle centered at the third guide pulley 342*d*.

The tension pulley 342*f*, the third guide pulley 342*d*, and the fourth guide pulley 342*e* are arranged in this order from the proximal end 31*b* of the shaft 31 side toward the driven member 332. The tension pulley 342*f* is arranged to bias a straight portion of the second part 72*b* of the elongated element 72 between the proximal end 31*b* of the shaft 31 and the third guide pulley 342*d*. The third guide pulley 342*d* is arranged such that the second part 72*b* of the elongated element 72 drawn from the proximal end 31*b* of the shaft 31 is guided through the tension pulley 342*f* toward the fourth guide pulley 342*e* by being bent approximately at an angle equal to or larger than 90° and smaller than 180°. In addition, the third guide pulley 342*d* is provided at a position separated from the proximal end 31*b* of the shaft 31 in the direction intersecting the axial direction (Z direction) of the shaft 31 and guides, in the direction along the rotational axis A2 (A7) of the driven member 332, the second part 72*b* of the elongated element 72 pulled out from the proximal end 31*b* of the shaft 31 in the direction intersecting the axial direction of the shaft 31. The fourth guide pulley 342*e* is arranged such that the second part 72*b* of the elongated element 72 guided from the third guide pulley 342*d* is guided toward the driven member 332 by being bent at an angle of approximately 90°. Accordingly, the second part 72*b* of the elongated element 72 can be guided at an angle with which the second part 72*b* can be easily wound around the driven member 332.

Each of the first guide pulley 342*a*, the second guide pulley 342*b*, and the tension pulley 342*c* and the corresponding one of the third guide pulley 342*d*, the fourth guide pulley 342*e*, and the tension pulley 342*f* are provided at positions substantially symmetric to each other with the driven member 332 interposed therebetween.

As illustrated in FIGS. 8 and 9, the driven member 332 includes a winding member 332*a* around which the first part 72*a* and the second part 72*b* of the elongated element 72 are wound, and a drive receiving member 332*b* that receives drive of the driving apparatus 90 for rotating the winding member 332*a*. The winding member 332*a* is a rotation member rotatable about the rotational axis A7 orthogonal to the second surface 33*ab* of the base 33*a*. The winding member 332*a* includes a winding part 332*aa* and a gear part 332*ab*. The winding part 332*aa* protrudes from the first surface 33*aa* of the base 33*a* so that the first part 72*a* and the second part 72*b* of the elongated element 72 guided through the shaft 31 are wound around the winding part 332*aa*. The gear part 332*ab* is provided between the first surface 33*aa* of the base 33*a* and the second surface 33*ab*. The drive receiving member 332*b* is a rotation member facing the second surface 33*ab* of the base 33*a* and rotatable about the rotational axis A2 orthogonal to the second surface 33*ab* of the base 33*a*. The drive receiving member 332*b* includes the above-described surface 33*ca* that receives drive and the first engagement portion 33*cb*. The drive receiving member 332*b* also includes a gear part 332*ba*. The winding member 332*a* and the drive receiving member 332*b* are not coaxially arranged.

The winding member 332*a* and the drive receiving member 332*b*, which are not coaxially arranged, are connected with each other through a gear part 352 as a drive transferring member between the winding member 332*a* and the drive receiving member 332b. Accordingly, drive power received by the drive receiving member 332b can be reliably transferred to the winding member 332a through the gear part 352. The gear part 352 includes a first gear part 352a engaged with the gear part 332ba of the drive receiving member 332b, and a second gear part 352b engaged with the gear part 332ab of the winding member 332a. The first gear part 352a and the second gear part 352b of the gear part 352 are coupled with each other to be integrally rotated. In the surgical instrument 30, the first gear part 352a of the gear part 352 engaged with the gear part 332ba of the drive receiving member 332b is rotated as the drive receiving member 332b of the driven member 332 is rotated by the driving apparatus 90. As a result, the second gear part 352b coupled with the first gear part 352a of the gear part 352 is rotated, and the winding member 332a of the driven member 332 engaged with the second gear part 352b of the gear part 352 is rotated. Accordingly, the first part 72a and the second part 72b of the elongated element 72 wound around the winding member 332a of the driven member 332 are operated, and the second jaw 32ab of the end effector 32 coupled with the first part 72a and the second part 72b of the elongated element 72 are opened and closed. The gear part 352 is an exemplary "gear member" in the claims.

The gear part 352 is arranged such that the rotational axis A3 of the driven member 333 for rotating the wrist part 32b of the end effector 32 is coaxial with the rotational axis. Accordingly, the gear part 352 and the driven member 333 are collectively arranged at one place, which leads to downsizing of the surgical instrument 30. Rotation of the gear part 352 is separated from the driven member 333 through, for example, a bearing. The gear part 352 is separated from the driven member 333 so that the driven member 333 does not rotate when the gear part 352 rotates. Accordingly, independence of drive of the driven member 332 can be maintained while the surgical instrument 30 is downsized.

<Configuration for Rotating Wrist Part>

Figure 10:
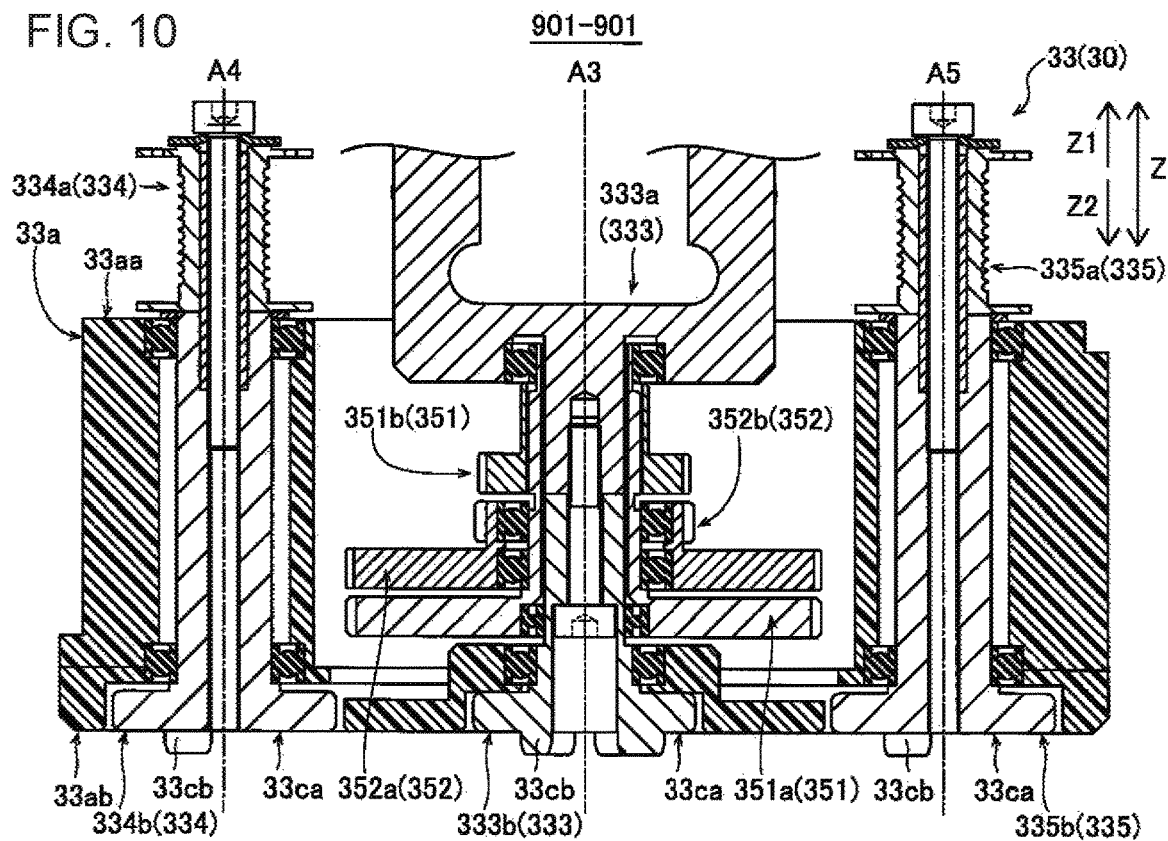
FIG. 10 is a diagram illustrating a schematic cross-sectional view along line 901-901 in FIG. 8.

As illustrated in FIGS. 8 to 10, the driven member 333 includes a coupling member 333a coupled with the torque transferring tube 80, and a drive receiving member 333b that faces the second surface 33ab of the base 33a and receives drive of the driving apparatus 90 for rotating the coupling member 333a. The coupling member 333a and the drive receiving member 333b are coaxially arranged and provided to be rotatable about the rotational axis A3 orthogonal to the second surface 33ab of the base 33a. The coupling member 333a protrudes from the first surface 33aa of the base 33a to be coupled with the torque transferring tube 80 guided through the shaft 31. The drive receiving member 333b includes the above-described surface 33ca that receives drive and the first engagement portion 33cb.

In the surgical instrument 30, the coupling member 333a together with the drive receiving member 333b is rotated as the drive receiving member 333b of the driven member 333 is rotated by the driving apparatus 90. As a result, the torque transferring tube 80 coupled with the coupling member 333a of the driven member 333 is rotated, and the wrist part 32b coupled with the torque transferring tube 80 is rotated. In this case, the end effector member 32a (the first jaw 32aa and the second jaw 32ab) coupled with the wrist part 32b is rotated together with the wrist part 32b.

In the surgical instrument 30, the coupling member 333a of the driven member 333 is coupled with the winding member 331a of the driven member 331 and the winding member 332a of the driven member 332. Specifically, when rotating, the driven member 333 rotates the winding member 331a of the driven member 331 and the winding member 332a of the driven member 332 coupled therewith about the rotational axis A3. Accordingly, not only the first jaw 32aa and the second jaw 32ab but also the elongated element 71 for driving the first jaw 32aa and the elongated element 72 for driving the second jaw 32ab can be rotated at rotation of the wrist part 32b. Accordingly, the occurrence of torsion to the elongated elements 71 and 72 can be reduced at rotation of the wrist part 32b. The driven member 333 rotates the winding member 331a of the driven member 331 and the winding member 332a of the driven member 332 about the rotational axis A3 while their relative positions are maintained.

Since the gear part 331ab of the winding member 331a of the driven member 331 (the gear part 332ab of the winding member 332a of the driven member 332) and the second gear part 351b of the gear part 351 (the second gear part 352b of the gear part 352) are engaged with each other, the winding member 331a of the driven member 331 (the winding member 332a of the driven member 332) rotates about the rotational axis A6 (the rotational axis A7) when the winding member 331a of the driven member 331 (the winding member 332a of the driven member 332) is rotated about the rotational axis A3 while the gear part 351 (the gear part 352) is fixed. In this case, the first jaw 32aa (the second jaw 32ab) can be unintentionally opened and closed, which is disadvantage.

Thus, in the surgical instrument 30, when the winding member 331a of the driven member 331 (the winding member 332a of the driven member 332) rotates about the rotational axis A3 through rotation of the driven member 333, the gear part 351 (the gear part 352) and the drive receiving member 331b (the drive receiving member 332b) are slave-rotated so that the winding member 331a of the driven member 331 (the winding member 332a of the driven member 332) does not rotate about the rotational axis A6 (the rotational axis A7) along with the rotation. In this case, the driving member 90c of the driving apparatus 90 (the driving member 90c including the second engagement portion 90a) corresponding to the driven member 331 (the driven member 332) is slave-rotated along with the slave rotation of the drive receiving member 331b (the drive receiving member 332b). In other words, the surgical instrument 30 is configured such that the winding member 331a of the driven member 331 (the winding member 332a of the driven member 332) does not rotate about the rotational axis A6 (the rotational axis A7) along with rotation of the winding member 331a of the driven member 331 (the winding member 332a of the driven member 332) about the rotational axis A3. Accordingly, the first jaw 32aa (the second jaw 32ab) is prevented from being unintentionally opened and closed.

In addition, as illustrated in FIG. 8, a distance W1 between two elongated elements 70 (the first part 71a and the second part 71b of the elongated element 71) provided to sandwich the winding member 331a of the driven member 331 rotated along with rotation of the driven member 333 is larger than a distance W2 between two elongated elements 70 (the first part 71a of the elongated element 71 and the second part 72b of the elongated element 72) provided not to sandwich the winding member 331a of the driven member 331. Accordingly, a space for providing the winding member 331a of the driven member 331 can be easily obtained between the two elongated elements 70 provided to sandwich the winding member 331a of the driven member 331. Since the distance W2 between the two elongated elements 70 provided not to sandwich the winding member 331a of the driven member 331 is smaller than the distance W1 between the two elongated elements 70 provided to sandwich the winding member 331a of the driven member 331, it is possible to prevent increase of a space for providing the two elongated elements 70 that do not need a space for providing the winding member 331a of the driven member 331. With these results, increase in the size of the surgical instrument 30 due to the elongated elements 70 can be prevented while a space for providing the winding member 331a of the driven member 331 is easily obtained. The same applies to the winding member 332a of the driven member 332 although detailed description thereof is omitted.

<Configuration for Bending First Multi-Articulated Part>

As illustrated in FIGS. 6 and 7, the first part 73a and the second part 73b of the elongated element 73 guided through the shaft 31 are wound around the driven member 334. The interface 33 is also provided with a fifth guide pulley 344a and a sixth guide pulley 344b that guide the first part 73a of the elongated element 73. The fifth guide pulley 344a is arranged between the proximal end 31b of the shaft 31 and the driven member 334 and provided to guide the first part 73a of the elongated element 73 drawn from the proximal end 31b of the shaft 31 toward the sixth guide pulley 344b in a direction (the Z direction) along the rotational axis A4 of the driven member 334. The sixth guide pulley 344b is arranged between the fifth guide pulley 344a and the driven member 334 and provided to guide the first part 73a of the elongated element 73 guided by the fifth guide pulley 344a toward the driven member 334 in a direction intersecting the rotational axis A4 of the driven member 334. With this configuration, the driven member 334 can be arranged such that the axis thereof is aligned with the direction along the longitudinal direction (Z direction) of the surgical instrument 30 and thus can receive drive of the driving apparatus 90 from the second surface 33ab side of the base 33a, and accordingly, the surgical instrument 30 can be easily mounted on the driving apparatus 90 by moving the surgical instrument 30 in the direction along the longitudinal direction of the surgical instrument 30. In addition, the first part 73a of the elongated element 73 can be easily wound around the driven member 334 while the driven member 334 around which the first part 73a of the elongated element 73 is wound is provided at a position separated from the proximal end 31b of the shaft 31 in the direction intersecting the axial direction (Z direction) of the shaft 31 at the proximal end 31b.

The interface 33 is also provided with a tension pulley 344c that is arranged between the proximal end 31b of the shaft 31 and the fifth guide pulley 344a and biases the first part 73a of the elongated element 73. Accordingly, the tension of the first part 73a of the elongated element 73 can be adjusted by the tension pulley 344c, and thus the occurrence of slack to the first part 73a of the elongated element 73 can be reduced when the direction in which the first part 73a of the elongated element 73 extends is changed by the fifth guide pulley 344a and the sixth guide pulley 344b. In addition, since the tension pulley 344c is provided on the path of the first part 73a of the elongated element 73 from the proximal end 31b of the shaft 31 to the driven member 334, no large space is needed to provide the tension pulley 344c, which leads to downsizing of the surgical instrument 30.

The tension pulley 344c is movable in the circumferential direction of a circle centered at the fifth guide pulley 344a. Accordingly, when force that the tension pulley 344c receives from the first part 73a of the elongated element 73 is larger than the biasing force of the tension pulley 344c because the tension of the first part 73a of the elongated element 73 is large, the tension pulley 344c can be moved in one of directions along the circumferential direction as if the tension pulley 344c were pressed from the first part 73a of the elongated element 73. As a result, excessively large biasing force can be prevented from being applied to the elongated element 73. When force that the tension pulley 344c receives from the first part 73a of the elongated element 73 is smaller than the biasing force of the tension pulley 344c because the tension of the first part 73a of the elongated element 73 is small, the tension pulley 344c can be moved in the other direction along the circumferential direction as if the tension pulley 344c pressed the first part 73a of the elongated element 73. As a result, excessively small biasing force can be prevented from being applied to the elongated element 73. With these results, tension applied to the first part 73a of the elongated element 73 can be stabilized. The tension pulley 344c receives biasing force by an elastic member such as a line spring and biases the first part 73a of the elongated element 73 in the circumferential direction of a circle centered at the fifth guide pulley 344a.

The tension pulley 344c, the fifth guide pulley 344a, and the sixth guide pulley 344b are arranged in this order from the proximal end 31b of the shaft 31 side toward the driven member 334. The tension pulley 344c is arranged to bias a straight portion of the first part 73a of the elongated element 73 between the proximal end 31b of the shaft 31 and the fifth guide pulley 344a. The fifth guide pulley 344a is arranged such that the first part 73a of the elongated element 73 drawn from the proximal end 31b of the shaft 31 through the tension pulley 344c is guided toward the sixth guide pulley 344b by being bent approximately at an angle equal to or larger than 90° and smaller than 180°. In addition, the fifth guide pulley 344a is provided at a position separated from the proximal end 31b of the shaft 31 in the direction intersecting the axial direction (Z direction) of the shaft 31 and guides, in the direction along the rotational axis A4 of the driven member 334, the first part 73a of the elongated element 73 pulled out from the proximal end 31b of the shaft 31 in the direction intersecting the axial direction of the shaft 31. The sixth guide pulley 344b is arranged such that the first part 73a of the elongated element 73 guided from the fifth guide pulley 344a is guided toward the driven member 334 by being bent at an angle of approximately 90°. Accordingly, the first part 73a of the elongated element 73 can be guided at an angle with which the first part 73a can be easily wound around the driven member 334.

The interface 33 is also provided with, for the second part 73b of the elongated element 73, a configuration similar to that of the first part 73a of the elongated element 73 described above. Specifically, the interface 33 is provided with a seventh guide pulley 344d and an eighth guide pulley 344e that guide the second part 73b of the elongated element 73. The seventh guide pulley 344d is arranged between the proximal end 31b of the shaft 31 and the driven member 334 and provided to guide the second part 73b of the elongated element 73 drawn from the proximal end 31b of the shaft 31 toward the eighth guide pulley 344e in the direction (Z direction) along the rotational axis A4 of the driven member 334. In addition, the eighth guide pulley 344e is arranged between the seventh guide pulley 344d and the driven member 334 and provided to guide the second part 73b of the elongated element 73 guided by the seventh guide pulley 344d toward the driven member 334 in the direction intersecting the rotational axis A4 of the driven member 334. With this configuration, the driven member 334 can be arranged such that the axis thereof is aligned with the direction along the longitudinal direction (Z direction) of the surgical instrument 30 and thus can receive drive of the driving apparatus 90 from the second surface 33ab side of the base 33a, and accordingly, the surgical instrument 30 can be easily mounted on the driving apparatus 90 by moving the surgical instrument 30 in the direction along the longitudinal direction of the surgical instrument 30. In addition, the second part 73b of the elongated element 73 can be easily wound around the driven member 334 while the driven member 334 around which the second part 73b of the elongated element 73 is wound is provided at a position separated from the proximal end 31b of the shaft 31 in the direction intersecting the axial direction (Z direction) of the shaft 31 at the proximal end 31b.

The interface 33 is also provided with a tension pulley 344f that is arranged between the proximal end 31b of the shaft 31 and the seventh guide pulley 344d and biases the second part 73b of the elongated element 73. Accordingly, the tension of the second part 73b of the elongated element 73 can be adjusted by the tension pulley 344f, and thus the occurrence of slack to the second part 73b of the elongated element 73 can be reduced when the direction in which the second part 73b of the elongated element 73 extends is changed by the seventh guide pulley 344d and the eighth guide pulley 344e. In addition, since the tension pulley 344f is provided on the path of the second part 73b of the elongated element 73 from the proximal end 31b of the shaft 31 to the driven member 334, no large space is needed to provide the tension pulley 344f, which leads to downsizing of the surgical instrument 30.

The tension pulley 344f is movable in the circumferential direction of a circle centered at the seventh guide pulley 344d. Accordingly, when force that the tension pulley 344f receives from the second part 73b of the elongated element 73 is larger than the biasing force of the tension pulley 344f because the tension of the second part 73b of the elongated element 73 is large, the tension pulley 344f can be moved in one of directions along the circumferential direction as if the tension pulley 344f were pressed from the second part 73b of the elongated element 73. As a result, excessively large biasing force can be prevented from being applied to the elongated element 73. When force that the tension pulley 344f receives from the second part 73b of the elongated element 73 is smaller than the biasing force of the tension pulley 344f because the tension of the second part 73b of the elongated element 73 is small, the tension pulley 344f can be moved in the other direction along the circumferential direction as if the tension pulley 344f pressed the second part 73b of the elongated element 73. As a result, excessively small biasing force can be prevented from being applied to the elongated element 73. With these results, tension applied to the second part 73b of the elongated element 73 can be stabilized. The tension pulley 344f receives biasing force by an elastic member such as a line spring and biases the second part 73b of the elongated element 73 in the circumferential direction of a circle centered at the seventh guide pulley 344d.

The tension pulley 344f, the seventh guide pulley 344d, and the eighth guide pulley 344e are arranged in this order from the proximal end 31b of the shaft 31 side toward the driven member 334. The tension pulley 344f is arranged to bias a straight portion of the second part 73b of the elongated element 73 between the proximal end 31b of the shaft 31 and the seventh guide pulley 344d. The seventh guide pulley 344d is arranged such that the second part 73b of the elongated element 73 drawn from the proximal end 31b of the shaft 31 through the tension pulley 344f is guided toward the eighth guide pulley 344e by being bent approximately at an angle equal to or larger than 90° and smaller than 180°. In addition, the seventh guide pulley 344d is provided at a position separated from the proximal end 31b of the shaft 31 in the direction intersecting the axial direction (Z direction) of the shaft 31 and guides, in the direction along the rotational axis A4 of the driven member 334, the second part 73b of the elongated element 73 pulled out from the proximal end 31b of the shaft 31 in the direction intersecting the axial direction of the shaft 31. The eighth guide pulley 344e is arranged such that the second part 73b of the elongated element 73 guided from the seventh guide pulley 344d is guided toward the driven member 334 by being bent at an angle of approximately 90°. Accordingly, the second part 73b of the elongated element 73 can be guided at an angle with which the second part 73b can be easily wound around the driven member 334.

Each of the fifth guide pulley 344a, the sixth guide pulley 344b, and the tension pulley 344c and the corresponding one of the seventh guide pulley 344d, the eighth guide pulley 344e, and the tension pulley 344f are provided at positions substantially symmetric to each other with the driven member 334 interposed therebetween.

As illustrated in FIGS. 8 and 10, the driven member 334 includes a winding member 334a around which the first part 73a and the second part 73b of the elongated element 73 are wound, and a drive receiving member 334b that faces the second surface 33ab of the base 33a and receives drive of the driving apparatus 90 for rotating the winding member 334a. The winding member 334a and the drive receiving member 334b are coaxially arranged and provided to be rotatable about the rotational axis A4 orthogonal to the second surface 33ab of the base 33a. The winding member 334a protrudes from the first surface 33aa of the base 33a so that the first part 73a and the second part 73b of the elongated element 73 guided through the shaft 31 are wound around the winding member 334a. The drive receiving member 334b includes the above-described surface 33ca that receives drive and the first engagement portion 33cb.

In the surgical instrument 30, the winding member 334a is rotated together with the drive receiving member 334b as the drive receiving member 334b of the driven member 334 is rotated by the driving apparatus 90. As a result, the first part 73a and the second part 73b of the elongated element 73 wound around the winding member 334a of the driven member 334 are operated, and the first multi-articulated part 32ca of the end effector 32 coupled with the first part 73a and the second part 73b of the elongated element 73 is bent.

<Configuration for Bending Second Multi-Articulated Part>

A configuration for bending the second multi-articulated part 32cb of the end effector 32 is substantially same as the above-described configuration for bending the first multi-articulated part 32ca of the end effector 32. Specifically, as illustrated in FIGS. 6 and 7, the first part 74a and the second part 74b of the elongated element 74 guided through the shaft 31 are wound around the driven member 335. The interface 33 is also provided with a fifth guide pulley 345a and a sixth guide pulley 345b that guide the first part 74a of the elongated element 74. The fifth guide pulley 345a is arranged between the proximal end 31b of the shaft 31 and the driven member 335 and provided to guide the first part 74a of the elongated element 74 drawn from the proximal end 31b of the shaft 31 toward the sixth guide pulley 345b in a direction (the Z direction) along the rotational axis A5 of the driven member 335. The sixth guide pulley 345b is arranged between the fifth guide pulley 345a and the driven member 335 and provided to guide the first part 74a of the elongated element 74 guided by the fifth guide pulley 345*a* toward the driven member 335 in a direction intersecting the rotational axis A5 of the driven member 335. With this configuration, the driven member 335 can be arranged such that the axis thereof is aligned with the direction along the longitudinal direction (Z direction) of the surgical instrument 30 and thus can receive drive of the driving apparatus 90 from the second surface 33*ab* side of the base 33*a*, and accordingly, the surgical instrument 30 can be easily mounted on the driving apparatus 90 by moving the surgical instrument 30 in the direction along the longitudinal direction of the surgical instrument 30. In addition, the first part 74*a* of the elongated element 74 can be easily wound around the driven member 335 while the driven member 335 around which the first part 74*a* of the elongated element 74 is wound is provided at a position separated from the proximal end 31*b* of the shaft 31 in the direction intersecting the axial direction (Z direction) of the shaft 31 at the proximal end 31*b*.

The interface 33 is also provided with a tension pulley 345*c* that is arranged between the proximal end 31*b* of the shaft 31 and the fifth guide pulley 345*a* and biases the first part 74*a* of the elongated element 74. Accordingly, the tension of the first part 74*a* of the elongated element 74 can be adjusted by the tension pulley 345*c*, and thus the occurrence of slack to the first part 74*a* of the elongated element 74 can be reduced when the direction in which the first part 74*a* of the elongated element 74 extends is changed by the fifth guide pulley 345*a* and the sixth guide pulley 345*b*. In addition, since the tension pulley 345*c* is provided on the path of the first part 74*a* of the elongated element 74 from the proximal end 31*b* of the shaft 31 to the driven member 335, no large space is needed to provide the tension pulley 345*c*, which leads to downsizing of the surgical instrument 30.

The tension pulley 345*c* is movable in the circumferential direction of a circle centered at the fifth guide pulley 345*a*. Accordingly, when force that the tension pulley 345*c* receives from the first part 74*a* of the elongated element 74 is larger than the biasing force of the tension pulley 345*c* because the tension of the first part 74*a* of the elongated element 74 is large, the tension pulley 345*c* can be moved in one of directions along the circumferential direction as if the tension pulley 345*c* were pressed from the first part 74*a* of the elongated element 74. As a result, excessively large biasing force can be prevented from being applied to the elongated element 74. When force that the tension pulley 345*c* receives from the first part 74*a* of the elongated element 74 is smaller than the biasing force of the tension pulley 345*c* because the tension of the first part 74*a* of the elongated element 74 is small, the tension pulley 345*c* can be moved in the other direction along the circumferential direction as if the tension pulley 345*c* pressed the first part 74*a* of the elongated element 74. As a result, excessively small biasing force can be prevented from being applied to the elongated element 74. With these results, tension applied to the first part 74*a* of the elongated element 74 can be stabilized. The tension pulley 345*c* receives biasing force by an elastic member such as a line spring and biases the first part 74*a* of the elongated element 74 in the circumferential direction of a circle centered at the fifth guide pulley 345*a*.

The tension pulley 345*c*, the fifth guide pulley 345*a*, and the sixth guide pulley 345*b* are arranged in this order from the proximal end 31*b* of the shaft 31 side toward the driven member 335. The tension pulley 345*c* is arranged to bias a straight portion of the first part 74*a* of the elongated element 74 between the proximal end 31*b* of the shaft 31 and the fifth guide pulley 345*a*. The fifth guide pulley 345*a* is arranged such that the first part 74*a* of the elongated element 74 drawn from the proximal end 31*b* of the shaft 31 through the tension pulley 345*c* is guided toward the sixth guide pulley 345*b* by being bent approximately at an angle equal to or larger than 90° and smaller than 180°. In addition, the fifth guide pulley 345*a* is provided at a position separated from the proximal end 31*b* of the shaft 31 in the direction intersecting the axial direction (Z direction) of the shaft 31 and guides, in the direction along the rotational axis A5 of the driven member 335, the first part 74*a* of the elongated element 74 pulled out from the proximal end 31*b* of the shaft 31 in the direction intersecting the axial direction of the shaft 31. The sixth guide pulley 345*b* is arranged such that the first part 74*a* of the elongated element 74 guided from the fifth guide pulley 345*a* is guided toward the driven member 335 by being bent at an angle of approximately 90°. Accordingly, the first part 74*a* of the elongated element 74 can be guided at an angle with which the first part 74*a* can be easily wound around the driven member 335.

The interface 33 is also provided with, for the second part 74*b* of the elongated element 74, a configuration similar to that of the first part 74*a* of the elongated element 74 described above. Specifically, the interface 33 is provided with a seventh guide pulley 345*d* and an eighth guide pulley 345*e* that guide the second part 74*b* of the elongated element 74. The seventh guide pulley 345*d* is arranged between the proximal end 31*b* of the shaft 31 and the driven member 335 and provided to guide the second part 74*b* of the elongated element 74 drawn from the proximal end 31*b* of the shaft 31 toward the eighth guide pulley 345*e* in the direction (Z direction) along the rotational axis A5 of the driven member 335. The eighth guide pulley 345*e* is arranged between the seventh guide pulley 345*d* and the driven member 335 and provided to guide the second part 74*b* of the elongated element 74 guided by the seventh guide pulley 345*d* toward the driven member 335 in the direction intersecting the rotational axis A5 of the driven member 335. With this configuration, the driven member 335 can be arranged such that the axis thereof is aligned with the direction along the longitudinal direction (Z direction) of the surgical instrument 30 and thus can receive drive of the driving apparatus 90 from the second surface 33*ab* side of the base 33*a*, and accordingly, the surgical instrument 30 can be easily mounted on the driving apparatus 90 by moving the surgical instrument 30 in the direction along the longitudinal direction of the surgical instrument 30. In addition, the second part 74*b* of the elongated element 74 can be easily wound around the driven member 335 while the driven member 335 around which the second part 74*b* of the elongated element 74 is wound is provided at a position separated from the proximal end 31*b* of the shaft 31 in the direction intersecting the axial direction (Z direction) of the shaft 31 at the proximal end 31*b*.

The interface 33 is also provided with a tension pulley 345*f* that is arranged between the proximal end 31*b* of the shaft 31 and the seventh guide pulley 345*d* and biases the second part 74*b* of the elongated element 74. Accordingly, the tension of the second part 74*b* of the elongated element 74 can be adjusted by the tension pulley 345*f*, and thus the occurrence of slack to the second part 74*b* of the elongated element 74 can be reduced when the direction in which the second part 74*b* of the elongated element 74 extends is changed by the seventh guide pulley 345*d* and the eighth guide pulley 345*e*. In addition, since the tension pulley 345*f* is provided on the path of the second part 74*b* of the elongated element 74 from the proximal end 31*b* of the shaft 31 to the driven member 335, no large space is needed to provide the tension pulley 345f, which leads to downsizing of the surgical instrument 30.

The tension pulley 345f is movable in the circumferential direction of a circle centered at the seventh guide pulley 345d. Accordingly, when force that the tension pulley 345f receives from the second part 74b of the elongated element 74 is larger than the biasing force of the tension pulley 345f because the tension of the second part 74b of the elongated element 74 is large, the tension pulley 345f can be moved in one of directions along the circumferential direction as if the tension pulley 345f were pressed from the second part 74b of the elongated element 74. As a result, excessively large biasing force can be prevented from being applied to the elongated element 74. When force that the tension pulley 345f receives from the second part 74b of the elongated element 74 is smaller than the biasing force of the tension pulley 345f because the tension of the second part 74b of the elongated element 74 is small, the tension pulley 345f can be moved in the other direction along the circumferential direction as if the tension pulley 345f pressed the second part 74b of the elongated element 74. As a result, excessively small biasing force can be prevented from being applied to the elongated element 74. With these results, tension applied to the second part 74b of the elongated element 74 can be stabilized. The tension pulley 345f receives biasing force by an elastic member such as a line spring and biases the second part 74b of the elongated element 74 in the circumferential direction of a circle centered at the seventh guide pulley 345d.

The tension pulley 345f, the seventh guide pulley 345d, and the eighth guide pulley 345e are arranged in this order from the proximal end 31b of the shaft 31 side toward the driven member 335. The tension pulley 345f is arranged to bias a straight portion of the second part 74b of the elongated element 74 between the proximal end 31b of the shaft 31 and the seventh guide pulley 345d. The seventh guide pulley 345d is arranged such that the second part 74b of the elongated element 74 drawn from the proximal end 31b of the shaft 31 through the tension pulley 345f is guided toward the eighth guide pulley 345e by being bent approximately at an angle equal to or larger than 90° and smaller than 180°. In addition, the seventh guide pulley 345d is provided at a position separated from the proximal end 31b of the shaft 31 in the direction intersecting the axial direction (Z direction) of the shaft 31 and guides, in the direction along the rotational axis A5 of the driven member 335, the second part 74b of the elongated element 74 pulled out from the proximal end 31b of the shaft 31 in the direction intersecting the axial direction of the shaft 31. The eighth guide pulley 345e is arranged such that the second part 74b of the elongated element 74 guided from the seventh guide pulley 345d is guided toward the driven member 335 by being bent at an angle of approximately 90°. Accordingly, the second part 74b of the elongated element 74 can be guided at an angle with which the second part 74b can be easily wound around the driven member 335.

Each of the fifth guide pulley 345a, the sixth guide pulley 345b, and the tension pulley 345c and the corresponding one of the seventh guide pulley 345d, the eighth guide pulley 345e, and the tension pulley 345f are provided at positions substantially symmetric to each other with the driven member 335 interposed therebetween.

As illustrated in FIGS. 8 and 10, the driven member 335 includes a winding member 335a around which the first part 74a and the second part 74b of the elongated element 74 is wound, and a drive receiving member 335b that faces the second surface 33ab of the base 33a and receives drive of the driving apparatus 90 for rotating the winding member 335a. The winding member 335a and the drive receiving member 335b are coaxially arranged and provided to be rotatable about the rotational axis A5 orthogonal to the second surface 33ab of the base 33a. The winding member 335a protrudes from the first surface 33aa of the base 33a so that the first part 74a and the second part 74b of the elongated element 74 guided through the shaft 31 are wound around the winding member 335a. The drive receiving member 335b includes the above-described surface 33ca that receives drive and the first engagement portion 33cb.

In the surgical instrument 30, the winding member 335a is rotated together with the drive receiving member 335b as the drive receiving member 335b of the driven member 335 is rotated by the driving apparatus 90. As a result, the first part 74a and the second part 74b of the elongated element 74 wound around the winding member 335a of the driven member 335 are operated, and the second multi-articulated part 32cb of the end effector 32 coupled with the first part 74a and the second part 74b of the elongated element 74 is bent.

[Modifications]

The one or more embodiments described above are merely exemplary and not restrictive in any aspect. The scope of the invention is defined not by the one or more embodiments described above but by the claims, and includes all changes (modifications) in meaning and range equivalent to those of the claims.

For example, in one or more embodiments described above, five driven members are provided, but the invention is not limited thereto. In an embodiment, the number of driven members may be any number. Specifically, one driven member or a plurality of driven members other than five may be provided.

In addition, in one or more embodiments described above, tension pulleys are provided, but the invention is not limited thereto. In an embodiment, tension pulleys do not necessarily need to be provided.

In addition, in one or more embodiments described above, each tension pulley is arranged between a proximal end of a shaft and a first guide pulley, but the invention is not limited thereto. In an embodiment, the tension pulley may be provided at any position as long as the function of the tension pulley is achieved. For example, the tension pulley may be arranged between the first guide pulley and a second guide pulley.

In addition, in one or more embodiments described above, each tension pulley is provided to be movable in the circumferential direction of a circle centered at the first guide pulley, but the invention is not limited thereto. In an embodiment, the tension pulley may be movable in any direction as long as the function of the tension pulley is achieved. For example, the tension pulley may be provided to be movable in a direction intersecting (orthogonal to) an elongated element as a biasing target.

In addition, in one or more embodiments described above, the first guide pulley is arranged to guide the elongated element by bending it at an angle equal to or larger than 90° and smaller than 180°, but the invention is not limited thereto. In the invention, the elongated element may be bent at any angle by the first guide pulley as long as the function of the first guide pulley is achieved. For example, the first guide pulley may be arranged to guide the elongated element by bending it at an angle smaller than 90°.

In addition, in one or more embodiments described above, the second guide pulley is arranged to guide the elongated element by bending it at an angle of 90°, but the invention is not limited thereto. In an embodiment, the elongated element may be bent at any angle by the second guide pulley as long as the function of the second guide pulley is achieved. For example, the second guide pulley may be arranged to guide the elongated element by bending it at an angle smaller than 90°, or may be arranged to guide the elongated element by bending it at an angle larger than 90° and smaller than 180°.

In addition, in one or more embodiments described above, an end effector includes a multi-articulated part, but the invention is not limited thereto. In an embodiment, the end effector does not necessarily need to include the multi-articulated part. However, the end effector preferably includes the multi-articulated part to increase the degrees of freedom in movement of the end effector to improve easiness of a surgery.

In addition, in one or more embodiments described above, the multi-articulated part includes two multi-articulated parts of a first multi-articulated part and a second multi-articulated part, but the invention is not limited thereto. In an embodiment, the multi-articulated part does not necessarily need to include the two multi-articulated parts of the first multi-articulated part and the second multi-articulated part. The multi-articulated part may include three multi-articulated parts or more.

In addition, in one or more embodiments described above, a surface that receives drive of each driven member is provided at a second surface of a base, but the invention is not limited thereto. In an embodiment, the surface that receives drive of each driven member may be provided at a position other than the second surface of the base.

In addition, in one or more embodiments described above, the distance W1 (refer to FIG. 8) is larger than the distance W2 (refer to FIG. 8), but the invention is not limited thereto. In an embodiment, the distance W1 may be equal to the distance W2, or the distance W1 may be smaller than the distance W2.

In addition, in one or more embodiments described above, the winding member 331a of the driven member 331 and the winding member 332a of the driven member 332 are rotated together with the driven member 333, but the invention is not limited thereto. In an embodiment, the winding member 331a of the driven member 331 and the winding member 332a of the driven member 332 do not necessarily need to be rotated together with the driven member 333.

In addition, in one or more embodiments described above, the driven member 331 (driven member 332) includes the winding member 331a (332a) and the drive receiving member 331b (332b) connected with each other through the gear part 351 (352), but the invention is not limited thereto. In an embodiment, the winding member 331a (332a) and the drive receiving member 331b (332b) of the driven member 331 (driven member 332) may be coaxially provided and directly connected with each other. In this case, similarly to the driven members 334 and 335, the driven member 331 (driven member 332) may be rotated through no gear part.

The invention claimed is:

1. A surgical instrument comprising:
   a base with a first surface and a second surface;
   an end effector;
   an elongated element to drive the end effector;
   a flexible shaft with a distal end and a proximal end, the distal end being coupled with the end effector;
   a winding member that is provided to the base rotatably about a rotational axis orthogonal to the second surface and includes a part protruded from the first surface such that the elongated element drawn from the flexible shaft is wound around and fixed to the part of the winding member;
   a drive receiving member that is provided to face the second surface and be rotatable about a rotational axis orthogonal to the second surface, and is configured to receive drive for rotating the winding member;
   a first guide pulley that is arranged between the proximal end of the flexible shaft and the winding member and guides the elongated element;
   a second guide pulley that is arranged between the first guide pulley and the winding member and guides the elongated element; and
   a tension pulley that is arranged between the proximal end of the flexible shaft and the first guide pulley and is configured to bias the elongated element, wherein
   the first guide pulley guides the elongated element drawn from the proximal end of the flexible shaft toward the second guide pulley in a direction along the rotational axis of the winding member,
   the second guide pulley guides the elongated element guided by the first guide pulley toward the winding member in a direction intersecting the rotational axis of the winding member, and
   the tension pulley is provided to be movable in a circumferential direction of a circle centered at the first guide pulley.

2. The surgical instrument according to claim 1, wherein the first guide pulley is arranged at a position separated from the proximal end of the flexible shaft in a direction intersecting an axial direction of the flexible shaft and is configured such that the elongated element pulled out from the proximal end of the flexible shaft in the direction intersecting the axial direction of the flexible shaft is guided in the direction along the rotational axis of the winding member.

3. The surgical instrument according to claim 1, wherein the second guide pulley is arranged at a position where the second guide pulley bends the elongated element at an angle of approximately 90° to guide the elongated element from the first guide pulley toward the winding member.

4. The surgical instrument according to claim 1, wherein
   the second surface of the base of the surgical instrument is mounted on a driving apparatus by relatively moving the surgical instrument to the driving apparatus in the direction along the rotational axis of the drive receiving member, and
   in a state where the surgical instrument is mounted on the driving apparatus, the drive receiving member is configured to be driven by the driving apparatus to rotate the winding member.

5. The surgical instrument according to claim 1, wherein
   the drive receiving member includes a first engagement portion on a side of the second surface of the base, and
   the first engagement portion is engaged with a second engagement portion that is provided to a driving apparatus and is rotationally driven.

6. The surgical instrument according to claim 1, wherein
   the end effector includes a wrist part, and
   the wrist part is configured to be rolled with respect to the flexible shaft, and
   the surgical instrument further includes:
   a flexible torque transferring member with a first end and a second end, the first end being coupled with the wrist part;
   a coupling member that is provided to the base rotatably about a second rotational axis orthogonal to the second surface and is coupled with the second end of the torque transferring member; and a second drive receiving member that is arranged to face the second surface and be coaxial with the coupling member, and is configured to receive drive for rotating the coupling member.

7. The surgical instrument according to claim 1, wherein the end effector includes a bendable multi-articulated part, the surgical instrument further includes:

a second elongated element to bend the multi-articulated part;

a second winding member that is provided to the base rotatably about a third rotational axis orthogonal to the second surface and includes a part protruded from the first surface such that the second elongated element drawn from the flexible shaft is wound around and fixed to the part of the second winding member;

a fifth guide pulley that is arranged between the proximal end of the flexible shaft and the second winding member and guides the second elongated element; and a sixth guide pulley that is arranged between the fifth guide pulley and the second winding member and guides the second elongated element, the fifth guide pulley guides the second elongated element drawn from the proximal end of the flexible shaft toward the sixth guide pulley in a direction along the third rotational axis of the second winding member, and the sixth guide pulley guides the second elongated element guided by the fifth guide pulley toward the second winding member in a direction intersecting the third rotational axis.

8. A surgical instrument comprising:
a base with a first surface and a second surface;
an end effector;
an elongated element to drive the end effector;
a flexible shaft with a distal end and a proximal end, the distal end being coupled with the end effector;
a winding member that is provided to the base rotatably about a rotational axis orthogonal to the second surface and includes a part protruded from the first surface such that the elongated element drawn from the flexible shaft is wound around and fixed to the part of the winding member;
a drive receiving member that is provided to face the second surface and be rotatable about a rotational axis orthogonal to the second surface, and is configured to receive drive for rotating the winding member;
a first guide pulley that is arranged between the proximal end of the flexible shaft and the winding member and guides the elongated element; and
a second guide pulley that is arranged between the first guide pulley and the winding member and guides the elongated element, wherein
the first guide pulley guides the elongated element drawn from the proximal end of the flexible shaft toward the second guide pulley in a direction along the rotational axis of the winding member,
the second guide pulley guides the elongated element guided by the first guide pulley toward the winding member in a direction intersecting the rotational axis of the winding member,
the elongated element includes first and second parts between the end effector and the winding member,
the first guide pulley and the second guide pulley guide the first part of the elongated element, the surgical instrument further includes:
a third guide pulley that is arranged between the proximal end of the flexible shaft and the winding member and guides the second part of the elongated element; and
a fourth guide pulley that is arranged between the third guide pulley and the winding member and guides the second part of the elongated element,
the third guide pulley guides the second part drawn from the proximal end of the flexible shaft toward the fourth guide pulley in the direction along the rotational axis of the winding member, and
the fourth guide pulley guides the second part guided by the third guide pulley toward the winding member in the direction intersecting the rotational axis of the winding member.

9. A surgical instrument comprising:
a base with a first surface and a second surface;
an end effector that includes a wrist part;
an elongated element to drive the end effector;
a flexible torque transferring member with a first end and a second end, the first end being coupled with the wrist part;
a flexible shaft with a distal end and a proximal end, the distal end being coupled with the end effector;
a winding member that is provided to the base rotatably about a first rotational axis orthogonal to the second surface and includes a part protruded from the first surface such that the elongated element drawn from the flexible shaft is wound around and fixed to the part of the winding member;
a first drive receiving member that is provided to face the second surface and be rotatable about a second rotational axis orthogonal to the second surface, and is configured to receive drive for rotating the winding member;
a first guide pulley that is arranged between the proximal end of the flexible shaft and the winding member and guides the elongated element;
a second guide pulley that is arranged between the first guide pulley and the winding member and guides the elongated element;
a tension pulley that is arranged between the proximal end of the flexible shaft and the first guide pulley and is configured to bias the elongated element;
a coupling member that is provided to the base rotatably about a third rotational axis orthogonal to the second surface and is coupled with the second end of the torque transferring member;
a second drive receiving member that is arranged to face the second surface and be coaxial with the coupling member, and is configured to receive drive for rotating the coupling member; and
a gear member that is provided to be rotatable coaxially with the coupling member and is configured to transfer rotation of the first drive receiving member to the winding member, wherein
the tension pulley is provided to be movable in a circumferential direction of a circle centered at the first guide pulley.

10. The surgical instrument according to claim 9, wherein the winding member rotates about the second rotational axis together with the coupling member when the coupling member is driven to rotate through the second drive receiving member.

11. The surgical instrument according to claim 10, wherein the first drive receiving member is driven to rotate through the gear member when the winding member rotates together with the coupling member.

12. The surgical instrument according to claim 9, wherein the end effector includes a first jaw and a second jaw, and the first and second jaws are configured to be kept from being opened or closed when the coupling member is rotated through the second drive receiving member.

13. The surgical instrument according to claim 9, wherein the end effector includes a bendable multi-articulated part, and
the surgical instrument further includes:
  a second elongated element to bend the multi-articulated part;
  a second winding member that is provided to the base rotatably about a fourth rotational axis orthogonal to the second surface and includes a part protruded from the first surface such that the second elongated element drawn from the flexible shaft is wound around and fixed to the part of the second winding member;
  a third drive receiving member that is arranged to face the second surface and be coaxial with the second winding member, and is configured to receive drive for rotating the second winding member;
  a third guide pulley that is arranged between the proximal end of the flexible shaft and the second winding member and guides the second elongated element; and
  a fourth guide pulley that is arranged between the third guide pulley and the second winding member and guides the second elongated element.

14. A surgical instrument comprising:
a base with a first surface and a second surface;
an end effector including a first jaw and a second jaw;
a first elongated element including first and second parts to drive the first jaw;
a second elongated element including a third part and a fourth part to drive the second jaw;
a flexible shaft with a distal end and a proximal end, the distal end being coupled with the end effector;
a first winding member that is provided to the base rotatably about a first rotational axis orthogonal to the second surface and includes a part protruded from the first surface such that the first and second parts of the first elongated element drawn from the flexible shaft are wound around and fixed to the protruded part of the first winding member;
a second winding member that is provided to the base to be rotatable about a second rotational axis orthogonal to the second surface and includes a part protruded from the first surface such that the third and fourth parts of the second elongated element drawn from the flexible shaft are wound around and fixed to the protruded part of the second winding member;
first and second guide pulleys that are arranged between the proximal end of the flexible shaft and the first winding member and guide the first part of the first elongated element;
third and fourth guide pulleys that are arranged between the proximal end of the flexible shaft and the first winding member and guide the second part of the first elongated element;
fifth and sixth guide pulleys that are arranged between the proximal end of the flexible shaft and the second winding member and guide the third part of the second elongated element; and
seventh and eighth guide pulleys that are arranged between the proximal end of the flexible shaft and the second winding member and guide the fourth part of the second elongated element,
wherein a distance between the first part of the first elongated element guided by the first and second guide pulleys and the second part of the first elongated element guided by the third and fourth guide pulleys is larger than a distance between the first part of the first elongated element guided by the first and second guide pulleys and the third part of the second elongated element guided by the fifth and sixth guide pulleys.

* * * * *